United States Patent
Tomer

(10) Patent No.: US 10,012,658 B2
(45) Date of Patent: Jul. 3, 2018

(54) PLATELET ANALYSIS SYSTEM

(75) Inventor: Aaron Tomer, Beer Sheva (IL)

(73) Assignee: EMOSIS, Illkirch-Graffenstaden (FR)

( * ) Notice: Subject to any disclaimer, the term of this patent is extended or adjusted under 35 U.S.C. 154(b) by 183 days.

(21) Appl. No.: 13/981,001

(22) PCT Filed: Jan. 19, 2012

(86) PCT No.: PCT/IL2012/050016
§ 371 (c)(1),
(2), (4) Date: Jul. 22, 2013

(87) PCT Pub. No.: WO2013/042111
PCT Pub. Date: Mar. 28, 2013

(65) Prior Publication Data
US 2014/0038207 A1 Feb. 6, 2014

Related U.S. Application Data

(60) Provisional application No. 61/434,467, filed on Jan. 20, 2011.

(51) Int. Cl.
*G01N 33/86* (2006.01)
*G01N 33/564* (2006.01)
(Continued)

(52) U.S. Cl.
CPC ........... *G01N 33/86* (2013.01); *G01N 33/564* (2013.01); *G01N 33/566* (2013.01);
(Continued)

(58) Field of Classification Search
CPC ............. G01N 33/86; G01N 33/56966; G01N 33/564; G01N 33/566; G01N 2333/70557; G01N 2800/222
See application file for complete search history.

(56) References Cited

U.S. PATENT DOCUMENTS 5,763,201 A * 6/1998 Tomer .............. G01N 33/56966
435/7.21
5,939,275 A 8/1999 Tomer
(Continued)

FOREIGN PATENT DOCUMENTS

WO 200127617 A1 4/2001

OTHER PUBLICATIONS

Of Xiao et al. Platelet Activation With Unfractionated Heparin at Therapeutic Concentrations and Comparisons With a Low-Molecular-Weight Heparin and With a Direct Thrombin Inhibitor. Circulation 97: 251-256 (1998).*

Primary Examiner — Gailene Gabel
(74) Attorney, Agent, or Firm — Browdy and Neimark, P.L.L.C.

(57) ABSTRACT

A method for diagnosis of HIT (Heparin-induced thrombocytopenia) in a patient's serum or plasma sample and a system comprising kits for performing the method are provided, where the method involves incubating a patient's sample with and without heparin and normal control sample with and without heparin with a platelet-rich plasma (PRP) of an individual not having a platelet disorder and then incubating an aliquot of each sample with a first label for both heparin activated and non-heparin activated platelets and a second label for platelets activated by the heparin-immune complex formed in the patient sample. HIT is diagnosed when the difference between the amount of activated platelets from the patient's sample with and without heparin is substantially larger than the difference between the normal control sample with and without heparin.

18 Claims, 16 Drawing Sheets

(51) Int. Cl.
  *G01N 33/566* (2006.01)
  *G01N 33/569* (2006.01)
(52) U.S. Cl.
  CPC ............... *G01N 33/56966* (2013.01); *G01N 2333/70557* (2013.01); *G01N 2800/222* (2013.01)

(56) References Cited

U.S. PATENT DOCUMENTS

| | | | |
|---|---|---|---|
| 5,939,276 A * | 8/1999 | Tomer | 435/7.21 |
| 2002/0081624 A1 | 6/2002 | Billheimer et al. | |
| 2006/0024744 A1 * | 2/2006 | Mills et al. | 435/7.1 |
| 2012/0197697 A1 | 12/2012 | Abdelouahed et al. | |

* cited by examiner

Figure 8  Panels A and B represent the light scatter of the microbeads
Panels C represent the immunofluorescence of the microbeads

PLATELET ANALYSIS SYSTEM

FIELD OF THE INVENTION

The present invention relates to a platelet analysis system, including specific kits for the diagnosis of platelet-related clinical disorders, and optionally a platelet analyzer.

BACKGROUND OF THE INVENTION

Blood coagulation disorders are among the most prevalent clinical problems in the general population. Increased tendency for coagulation termed "Hypercoagulability" or "Thrombophilia" is a major cause of morbidity and mortality.

In the U.S. there are about 500,000 venous thrombosis events, with a conservative estimate of 100,000 deaths annually—greater than death occurrence related to AIDS, breast cancer and road accidents combined. In addition, 1.1 million myocardial infarctions, and more than 150,000 stroke deaths occur annually.

In cancer patients, thrombosis is the second leading cause of death, after the malignancy itself. Yet, therapy is given only after the occurrence of the thrombotic event.

In women, hypercoagulability is a major risk factor for pregnancy vascular complications including: thrombosis, severe preeclampsia, intra-uterine growth restriction and fetal death, and thrombosis following delivery or hormonal therapy. According to the recent literature, in developed countries the leading cause of death of women after delivery in pulmonary thrombo-embolism.

Another problem is the increased tendency for bleeding related to platelets, which is also common in the general population. About 25% of women with menorrhagia—increased menstrual bleeding—have such abnormality.

The major factor involved in pathogenesis of thrombosis and bleeding is the circulating blood platelets.

Properties of blood platelets may be measured by flow cytometry.

Flow cytometry (abbreviated: FCM) is a technique for counting and examining microscopic particles, such as cells, by suspending them in a stream of fluid and passing them by an electronic detection apparatus. It allows simultaneous multiparametric analysis of the physical and/or chemical characteristics of up to thousands of particles per second. Flow cytometry is routinely used in the diagnosis of health disorders such as blood cancers.

A beam of light (usually laser light) of a single wavelength is directed onto a hydrodynamically-focused stream of liquid. A number of detectors are aimed at the point where the stream passes through the light beam: one in line with the light beam (Forward Scatter or FSC) and several perpendicular to it (Side Scatter or SSC) and one or more fluorescent detectors. Each suspended particle from 0.2 to 150 micrometers passing through the beam scatters the ray, and fluorescent chemicals found in the particle or attached to the particle may be excited into emitting light at a longer wavelength than the light source. This combination of scattered and fluorescent light is picked up by the detectors, and, by analyzing fluctuations in light intensity at each detector (one for each fluorescent emission peak), it is then possible to derive various types of information about the physical and chemical structure of each individual particle. FSC correlates with the cell volume and SSC depends on the inner complexity of the particle (i.e., shape of the nucleus, the amount and type of cytoplasmic granules or the membrane roughness). This is because the light is scattered off of the internal components of the cell. See also: Tomer A [Tomer A 2004], [Tomer A et al., 1988], [Tomer A et al., 1989a] for further general introduction to FCM of blood.

Modern flow cytometers are able to analyze several thousand particles every second, in "real time," and can actively separate and isolate particles having specified properties. A flow cytometer is similar to a microscope, except that, instead of producing an image of the cell, flow cytometry offers "high-throughput" (for a large number of cells) automated quantification of set parameters. For further general introduction to cell isolation and analysis, see Tomer A [Tomer A, 2002], [Tomer A et al., 1987].

Modern instruments usually have multiple lasers and fluorescence detectors. Increasing the number of lasers and detectors allows for multiple antibody labeling, and can more precisely identify a target population by their phenotypic markers [Tomer A, 2004]

The data generated by flow-cytometers can be plotted in a single dimension, to produce a histogram, or in two-dimensional dot plots. The regions on these plots can be sequentially separated, based on fluorescence intensity, by creating a series of subset extractions, termed "gates."

The following publications describe tests performed on blood platelets, involving cell cytometry.

U.S. Pat. No. 5,656,442 to SCRIPPS RESEARCH NST [US] describes methods for characterizing platelet aggregation defects. In one example a Cam variant of Glanzmann's thrombasthenia is characterized as having a ligand binding defect. In another, a patient with myelofibrosis is identified as having an activation defect. Analysis is by fluorescence-activated flow cytometry. The system includes an enclosure containing, in separate containers: (a) activation specific ligand (ASL) that binds with activated platelets: (b) an activation independent ligand (AIL) that forms a ligand-induced binding site (LIBS) on normal platelets, wherein said activation independent ligand includes a polypeptide listing a sequence selected from the group consisting of RGD, LGGAKQAGDV (SEQ ID NO:1), and KQAGDV (SEQ ID NO:2): (c) an anti-LIBS antibody; and (d) a platelet agonist.

WO 03028627 to BERG DAVID and BERG LOIS HILL [US] describes a method including tests for determining levels of fibrinogen, prothrombin fragment 1+2, thrombin/antithrombin complexes, soluble fibrin monomer, and platelet activation by flow cytometry. Deviation from the normal values in any two of five assays is used to diagnose chronic fatigue syndrome, fibromyalgia, or other disease associated with activation of the coagulation response. No details are provided about measurement of the platelet activation.

US 2005214877 to PPD BIOMARKER DISCOVERY SCIENCES, LLC describes a method for measuring the amount of a platelet surface protein in a sample including platelets, including the steps of: (a) contacting the sample with a platelet stabilizing composition having an anticoagulant and at least one platelet activation inhibitor; (b) incubating the sample with a labeled compound having specific affinity for the platelet surface protein and a platelet stimulating factor; and (c) detecting labeled compound bound to platelets by cytometry (e.g. microvolume laser scanning cytometry), whereby the amount of the platelet surface protein may be measured.

US 2003194818 to HECHINGER MARK [US] describes immunoassay methods and apparatus which utilize flow cytometry, coated latex microspheres, and fluorochrome labeled antibodies, to simultaneously detect the presence and amount of one or more analytes in a sample. By combining FALS and fluorescence, beads of several different sizes, colors or shapes are used, each bead coated with a different analyte, for the simultaneous detection of one or more analytes and of cell components such as platelets in a sample.

US 2003032068 HECHINGER MARK [US] describes similar methods and apparatus, directed to platelet Ig positive control reagents and assays which provide for the setting of the fluorescence positive region for each patient. The platelet control is sized to fit between the platelets and red cells with the goal of making it ideal as a true biological control.

However, despite the clinical importance of platelet disorders there is yet an unmet need for platelet analysis systems and methods that would allow clinicians to easily diagnose various medical conditions related to platelets. Such conditions include both platelet functional abnormality, causing bleeding, and ongoing blood hypercoagulable activity, which may lead to vascular occlusion and thrombosis, and in pregnant women to placental vascular complications and fetal death. Currently used platelet analysis methods carry certain methodological and practical limitations, thus generally providing incomplete clinical information as is specified below.

Immune thrombocytopenia (IT) is a disorder characterized by antibody-mediated accelerated platelet destruction [George J N and Rizvi M A], [Tomer A et al. 1991]. Despite being a clinically important disorder its diagnosis is currently hampered by the lack of a feasible and reliable assay for routine clinical use. Thus, current diagnoses are generally based on clinical impressions deduced primarily by exclusion, see—[Neunert C et al.], [Provan D et al.], despite the patient presentations being sometimes complex.

Furthermore, suspected patients may be subjected to empiric therapies such as high dose corticosteroids that may carry significant side effects, or high dose intravenous immunoglobulins which is an expensive therapeutic option.

Methods to determine general anti-platelet or platelet bound antibody-similar to Coombs test for red-blood cells—have proven to be non-useful, since platelets unlike red cells express Fc-receptor and naturally bind circulating antibodies.

Current methods that may be used to determine autoimmune thrombocytopenia, such as an ELISA type assay (MAIPA), carry significant methodological and practical limitations, have limited specificity, are labor intensive (three-day work to obtain results) and require high expertise to obtain results [Chong B H, Keng T B], [Cines D B, Blanchette V S], [McMillan R, et al. 2003]. Thus they are not routinely available for diagnosis.

Further, these assays are not approved for the diagnosis of autoimmune thrombocytopenia.

For these reasons, no confirmatory laboratory assay is indicated or recommended by the American Society of Hematology [Neunert C et al.], [Provan D et al.] for the diagnosis of IT.

It is important to note that as indicated by Chong and Keng, however, the reason for not requiring a confirmatory test (as is required for example for the diagnosis of APS) is that there is not yet a reliable test with sufficiently high sensitivity and specificity. Furthermore, a diagnosis based on exclusion carries potential problems [Cines D B, Blanchette V S], [McMillan R, et al. 2003], thus a direct laboratory confirmation of the presence of circulating autoantibodies directed against platelet-specific receptors would be clinically helpful [Chong B H, Keng T B], [Cines D B, Blanchette V S], [McMillan R, et al. 2003]. The clinical effect of these antibodies is further highlighted by our previous studies [Tomer A, et al., 1989], [McMillan R. et al. 2004].

APS is an acquired hypercoagulable state affecting young and middle aged individuals. The syndrome is associated with arterial and venous thrombosis and in women, with recurrent fetal loss. The international diagnostic criteria require the occurrence of a clinical event, and the demonstration in the patient's blood of auto-antibodies reacting with natural phospholipids [Miyakis S, et al,]. Current laboratory assays for diagnosis are heterogeneous with methodological and practical limitations [Wong R C, Favaloro E J]. As stated in this reference "Despite numerous past and ongoing efforts, there remains significant variation in results from assays for the major antiphospholipid antibodies (aPL), namely anticardiolipin (aCL), anti-beta2 glycoprotein I (anti-beta2GPI), and lupus anticoagulant (LA)", and "However, because of the paucity of good-quality published evidence, there is a heavy reliance on expert opinion, and thus the existing consensus guidelines for aPL testing and reporting are largely eminence based rather than evidence based".

Another major problem is that the correlation of the laboratory findings with the clinical presentation is not entirely apparent. For example, according to several studies, about 15% to 17% of children with viral infection demonstrate APS false-positive test. In a recently reported study [de Groot], a world expert reported >30% misdiagnosis of APS samples sent by him to well established clinical laboratories. Regarding false positive and false negative results, see also [Merriman E et al.], [Aboud M et al.], [Pellegrino N M and Caccavo D], [Bizzaro N et al.], [Martorell J R et al.], [Koike T et al.], [Rusnak et al.], [Lakos G and Teodoescu M], [Moore G W et al.], [Pengo V et al.], [de Larrañaga G et al.], [Asherson et al.], [Zhu W F et al.], [Uthman I W et al.], [Bernard C et al.] for the methodological limitations, including false positive and false negative, etc. It is important to note that because of these methodological limitations of the routinely used laboratory tests, the international guidelines require the repetition of the assays 12 weeks apart when their outcome is positive [Miyakis S et al].

Heparin is the standard anti-coagulant therapy for the treatment and prevention of thrombosis. Heparin-induced thrombocytopenia and thrombosis (HIT) is an immune-mediated serious complication that may develop in patients sensitized to heparin. Approximately 5% of patients treated with full dose heparin develop HIT. About 50% of patients, who manifest HIT, develop thrombosis, half with severe morbidity and death. The diagnosis of HIT poses serious clinical dilemmas. At present, quick clinical decision is required to immediately discontinue heparin and start with an alternative anti-coagulant therapy, suitable for patients with HIT [Sheridan D, et al.], [Kelton J G, et al.], [Chong B H.], [Alving B.], [Aster R H.], [Thielmann M et al.]

Current methods based on the detection of antibodies against heparin-platelet-factor 4 complex such as the ELISA and the Gel-particle assay (e.g. PaGIA) have certain methodological and practical limitations.

Antibodies may be detected by these methods in up to 30% of patients treated with heparin, however, only 5% manifest clinical HIT [Sheridan D, et al.], [Kelton J G, et al.]. In addition, these assays have a range of >10% false-negative [Alving B.], [Arepally G, et al.,], [Hirsh J. et al.], [Visentin G P et al.], they detect only heparin-platelet factor 4 complex which is not formed in all patients. In addition, up to 80% false-positive results may occur in patients having autoimmune APS, i.e., the patient will carry life-long with unnecessary treatments on one hand and avoidance of required therapies on the other hand [Pauzner R, et al.].

The functional platelet aggregation assay (HIPA) is complex, requiring multiple normal donors (usually four), has a low sensitivity [Thielmann M et al.], [Chong B H et al.], [Favoloro E J et al.] and a low reproducibility. Furthermore, it involves platelet washing step, a manipulation known to cause platelet activation thus inevitably confounding the assay results.

The functional, radioactive serotonin-release assay (SRA) is considered the gold-standard, However, it is impractical and is not available out of limited research laboratories [Sheridan et al.], [Kelton J G et al.], [Alving B], [Arepally G et al.], [Visentin G P et al.], [Favoloro E J et al.]. Thus, to overcome these above mentioned limitations, we developed a practical, rapid, sensitive and specific functional flow cytometric method for the diagnosis of HIT. The functional method determines the capacity of patient's serum/plasma to induce platelet activation in presence of heparin—similar in concept to the gold-standard radioactive SRA.

Another method was described 15 years ago using flow cytometry [Tomer A, 1997]. However, because it has been found that this method requires high expertise, it is not available in regular clinical laboratories.

Defect in the hemostatic function of platelets leads to bleeding tendency-which not uncommon in the general population. Thus, testing of platelet function is an important clinical assessment.

Turbidometric aggregometry platelet function assessment method is a classic and most common method for testing platelet function, being used for approximately 50 years. It is based on stimulation of platelets in suspension and stirring with a magnet to form platelet aggregates, which allow more light transmission compared to full suspensions. A more modern instrument—though not very common—is the PFA100 of Siemens Co which imitates this reaction with a difference in the method of reading. The PFA-100 aspirates a blood specimen into disposable test cartridges through a microscopic aperture cut into a biologically active membrane at the end of a capillary. The membrane of the cartridges is coated with collagen and adenosine diphosphate (ADP) or collagen and epinephrine, inducing a platelet plug to form which closes the aperture.

The commonly employed methods use a relatively high-dose stimulant to achieve an end-point result, thus not being capable of testing the three phases of the platelet activation process leading to final aggregation, as the method described here does, which is important in diagnosis of platelet dysfunction.

In addition, the use of high-dose stimulants abrogates the possibility of detecting mild to moderate dysfunction such as occurs in platelet storage-pool disease [B S Coller and D L French], [Shattil S J et al.], [Fitzgerald R, Pirmohamed M.]. These methods also incapable of detecting some platelet functional disorder such as Scott syndrome and other ones [B S Coller and D L French], [Shattil S J et al].

Blood platelets play a pivotal role in normal hemostasis. Paramount to their function are membrane glycoproteins (GPs) that specify the critical ligand interactions involved in platelet adhesion and aggregation, necessary for normal hemostasis.

Congenital platelet dysfunctions are heritable bleeding disorders that may result from platelet glycoprotein-receptor abnormalities. As a consequence, these disorders are associated with excessive bleeding, especially from skin and mucosa. Bernard-Soulier syndrome and Glanzmann thrombasthenia are the major congenital disorders of platelet-receptor defects [B S Coller and D L French], [Shattil S J et al.], [Fitzgerald R, Pirmohamed M.].

Bernard-Soulier syndrome results from a defect in the GP Ib-IX (CD42) complex, which functions as a binding site for the von Willebrand factor (vWF), which in turn mediates platelet attachment to components of subendothelium, exposed by damage to the vessel wall [B S Coller and D L French], [Nurden A, Nurden P.], [Harold R Robert and Alice D Ma], [Shattil S J et al.].

This syndrome is also associated with thrombocytopenia. Therefore, it is frequently confused with Immune Thrombocytopenia (IT), as occurs for example with the index patient shown in FIGS. 13-14, who was planned for an unnecessary surgical procedure—splenectomy. It is important to note here that some platelet disorders as this require sometimes more than one test to achieve correct diagnosis-such as ruling out IT in the present case. Thus, the proposed Platelet Analysis System here is merely a one system for evaluation of platelet disorders.

Glanzmann thrombasthenia results from a defect in the major platelet functional receptor GPII/IIIa (CD41a), necessary for fibrinogen-mediated platelet aggregation [B S Coller and D L French], [Shattil S J et al.], [Fitzgerald R, Pirmohamed M.].

Aspirin inhibits the arachidonic acid pathway enzyme cyclooxygenase I, COX-I), which is required for the formation of the platelet prostaglandin stimulant, Thromboxane A2, in a coagulation process.

Thienopyridine agents specifically and irreversibly inhibit the $P2Y_{12}$ sub-type of ADP receptor, which is important in platelet activation and aggregation [Shattil S J et al.].

Current clinical guidelines recommend a chronic treatment with Platelet-inhibitory agents for all patients with coronary-artery disease (CAD), peripheral vascular disease (PVD), cerebro-vascular disease (CVD) that includes brain circulation limitations, patients with transient-ischemic-attack (TIA), or stroke; retinal vascular thrombosis in the eye, vascular angioplasty (such as coronary artery dilation by catheter—with or without stenting), and other categories of patients with risk of vascular occlusion and thrombosis.

Nevertheless, many patients with recurrent thrombosis have been found not to have adequate response to the inhibitory effect of these agents, a syndrome termed "Aspirin resistance" [Fitzgerald R, Pirmohamed M.], or "Clopidogrel resistance" [Qureshi Z, Hobson A R.].

There is need for a practical system for diagnosis that includes instrumentation and diagnostic kits. The proposed system should allow the performance of feasible and highly informative laboratory assays. The assays should be highly reliable and capable of providing useful medical information for the most common platelet-related disorders.

A special aim in the design of the system is to provide highly needed tests for the determination of circulating platelet activation markers as indicators of ongoing, in vivo, prothrombotic activity. These tests are not available by the commonly used platelet analysis methods in the clinical coagulation laboratories.

All proposed assays are optimized, simplified, refined and adjusted for daily routine use in clinical laboratories.

SUMMARY OF THE INVENTION

According to one aspect, systems and methods for comprehensive analysis of circulating blood platelets are provided, to be used for diagnosis of platelet-related disorders in routine clinical laboratories.

The systems include reagents, in the form of diagnostic kits designed for specific platelet analyses; the systems may further include dedicated, simple and easy to use instruments, such as cytometers, suitable for performing said analyses.

The analytical system is primarily intended for the testing of platelets or auto-antibodies or allo-antibodies reacting with platelets, in specific and important clinical conditions associated with platelet dysfunction and bleeding tendency, and hypercoagulability leading to thrombosis. In addition, testing of platelet functional capacity includes responsiveness to stimulants and inhibitors, and platelet activation markers as indicator of ongoing, in vivo prothrombotic activity. The system is also capable of diagnosis of specific medical conditions associated with immune and antibody-mediated platelet disorders such as immune thrombocytopenia.

Using the system, the testing method is especially applicable for testing of one or more of:

a. Platelet activation state in vivo, as a marker for ongoing prothrombotic activity (which may lead to thrombosis), in various clinical conditions including cardiovascular, cerebrovascular and peripheral vascular disease, diabetes, cancer, and pregnancy with a risk of vascular complications.

b. Specific antibody-mediated conditions including i) heparin-induced thrombocytopenia, ii) auto-immune thrombocytopenia (ITP), iii) allo-immune thrombocytopenia e.g. Neonatal-alloimmune thrombocytopenia-NAIT, iv) Post-transfusion purpura-PTP, and v) presence of anti-platelet-phospholipid autoantibodies in Anti-phospholipid Syndrome (APS).

c. Platelet functional capacity: Responsiveness to various stimulants (agonists)—quantitative assessment of inhibitory effect of anti-platelet drugs, widely used in clinical care of patients with cardiac and vascular diseases, including aspirin and clopidogrel—quantitative assessment;

d. Congenital functional platelet defects such as Bernard-Soulier syndrome and Glanzmann thrombasthenia, and other defects associated with bleeding disorder (tendency to excessively bleed).

Detection method: One basic diagnostic method includes performing standard flow cytometry—preferably using a relatively small, dedicated instrument. However the detection method may use other technologies for detecting antibody or protein (e.g. Annexin A5) binding, such as chemiluminescence, gel-particle agglutination assay, and Enzyme-linked Immunosorbent Assay (ELISA)/solid-phase assay with immobilization of antibody or antigen on material surface, or on plastic particles.

The detected signal may be indicative of fluorescence, light, color, or agglutination of particles.

Samples for testing could be of whole-blood or platelets, e.g. platelet-rich plasma (PRP), all fixed and non-fixed.

The systems and methods include assays of:
1. Platelet immunity including i) auto-immune thrombocytopenia (ITP), ii) allo-immune thrombocytopenia e.g. Neonatal-alloimmune thrombocytopenia-NAIT, and Post-transfusion purpura-PTP;
2. APLA/APS or Hughes syndrome (Anti-phospholipid-Antibody-Syndrome) for anti-platelet phospholipids auto-antibodies;
3. HIT (Heparin-induced thrombocytopenia), for capacity of patient's antibodies to cause platelet activation in presence of heparin;
4. Platelet function—including marking platelets indicating: i) response to stimulations of the major platelet functional receptor for platelet aggregation GPIIb/IIIa (CD41a), ii) platelet release reaction (in response to activation) of active mediators from platelet granules which enhance their activity, and iii) the expression of procoagulant activity i.e. the enhancement of thrombin generation and thrombotic process;
5. Platelet functional receptor deficiencies/abnormalities—e.g. Glanzmann thrombasthenia and Bernard-Soulier syndromes, and other heritable platelet dysfunctions;
6. Platelet function inhibition—measurement of the inhibitory effect of anti-platelet drugs on platelet function e.g. detecting resistance to Aspirin or Clopidogrel therapy—quantitative assay, and
7. Platelet activation markers in circulation as an indicator of ongoing, in vivo, prothrombotic activity.

The assay is especially applicable for patients having clinical conditions associated with high-risk for thrombosis, including:

Coronary artery disease (CAD) such as angina pectoris—stable or unstable, acute coronary syndrome (ACS)—or post myocardial infarction (MI); peripheral vascular disease (PVD), cerebro-vascular disease (CVD) including brain circulation conditions such as Transient-ischemic-attack (TIA), or stroke; diabetes—which is highly associated with vascular disease; hypertensive disorder of pregnancy including preeclampsia associated with thrombosis, fetal growth restriction and fetal death; thrombophilic risk-factors, including: Antiphospholipid Antibody syndrome (APS, APLA), FV-Leiden mutation, FIT mutation, anticoagulant protein deficiency: Protein C, protein S, and ATIII; ongoing prothrombotic activity prior to and after cessation of anticoagulant therapy such as warfarin, and cancer—for prediction of thrombosis and providing preventive measures.

It is important to note that there might be a high discrepancy between genotypic and phenotypic clinical presentations, thus functional determination of an active hypercoagulable state is required.

The overall purpose of these assays is clinical, to enable the identification of patients at risk, and to enable the physician to provide according to the test results.

Markers: the markers in the assays are suitable for detection by flow-cytometry (FCM) or chemiluminescence measurement methods, for example.

Platelet activation markers may be used, including platelet-related particles for expression of a) procoagulant activity—using Annexin A5 probe; thrombospondin, or fibrinogen binding; b) post release reaction—using anti p-selectin (CD62p), anti CD63, for example; c) activation of the GPIIb/IIIa (CD41a) receptor on platelet surface.

Platelet-monocyte (PMC), and platelet-granulocyte complexes may be formed, and detected using specific monoclonal antibodies for the diagnoses.

Markers for chemiluminescence measurement—may include markers of Platelet factor 4 (PF4) & Platelet β-thromboglobulin (β-TG), C-reactive protein (CRP), fibrin D-dimers, and activated platelet and platelet-related particles.

According to one aspect, a method for diagnosis of HIT (Heparin-induced thrombocytopenia) in a patient's serum or plasma sample is provided, the method comprising:
stage A comprising:
incubating a first PI (patient 1) sample consisting of: a first aliquot of the patient's sample with PRP of a first healthy individual, and a physiologically-compatible buffer, with the proviso that the buffer does not contain calcium nor magnesium ions;

incubating a first PIH (patient 1 with heparin) sample consisting of: a second aliquot of the patient's sample with said PRP, heparin and the buffer;

incubating a first NC (normal control) sample consisting of: a first aliquot of a plasma or serum sample of a healthy individual with said PRP, and the buffer;

incubating a first NCH (normal control with heparin) sample consisting of: a second aliquot of the plasma or serum sample of the healthy individual with said PRP, heparin and the buffer; stage B comprising:

incubating a second PI sample consisting of: an aliquot of the first PI sample, a second PIH sample consisting of: an aliquot of the first PIH sample, a second NC sample consisting of: an aliquot of the first NC sample, and a second NCH sample consisting of: an aliquot of the first NCH sample, each with: a first label, the first label capable of labeling both heparin activated and non-heparin activated platelets, a second label, the second label capable of labeling platelets activated by heparin and the buffer;

Stage C comprising:

measuring a similar amount of platelets in each of the second samples by measuring the first label, in each of the second samples;

measuring amounts of heparin-activated platelets by measuring the amount of second label on platelets activated by heparin, in each of said similar amount of platelets;

calculating differences between: amount of activated platelets from second PIH sample and amount of activated platelets from second PI sample, and between amount of activated platelets from second NCH sample and amount of activated platelets from second NC sample, and comparing said differences for said second PIH and second PI samples, and for said second NCH and said second NC sample, wherein HIT is diagnosed in the patient's sample when said difference for said second PIH and second PI samples is substantially larger than said difference for said second NCH and said second NC sample.

Said difference for said second PIH and second PI samples is selected to be substantially larger, for example, at least 2.5 times larger, than said difference for said second NCH and said second NC sample.

The first label is for example a label of platelet receptor GPIIb/IIIa.

In some embodiments, the second label is a fluorescence labeled monoclonal antibody against p-selectin CD62p expressed by the heparin-activated platelets, the method comprising measuring the intensity of fluorescence by the second label bound to the activated platelets.

The amounts of heparin-activated platelets may each be measured by said second label mean total fluorescence from total platelet population of each similar amount.

In some embodiments, the method further comprises:

calculating % of activated platelets by setting a marker on 2.5% (2SD of Normal distribution) of the high-CD62p-fluorescence end of the fluorescence measurement of the similar amount of NC;

calculating the difference in reading between %-activated platelets in PIH and %-activated platelets in PI, and the difference in reading between %-activated platelets in NCH and %-activated platelets in NC, at said high—CD62p fluorescence end, and Comparing said differences for PIH and PI to NCH and NC samples, wherein positive results are difference for PIH and PI substantially more than the NCH and NC difference.

The difference for PIH and PI is for example over 2.5 times more than the NCH and NC difference.

In preferred embodiments, the plasma or serum samples are not more than 10 µL.

Stage B preferably further comprises: incubating a TRAP sample consisting of: TRAP, the first label, the second label, and the buffer, and Stage C further comprises measuring the amount of activated platelets in the TRAP sample.

In some embodiments, Stage A may further comprise:

incubating a first PC (positive control) sample consisting of: a first aliquot of a plasma or serum sample of an individual having HIT, with said PRP, and the buffer;

incubating a first PCH sample consisting of: a first aliquot of a plasma or serum sample of an individual having HIT, with heparin, said PRP, and the buffer;

and stage B further comprises:

incubating a second PC sample consisting of: an aliquot of the first PC sample, and a second PCH sample consisting of: an aliquot of the first PCH sample, each with: the first label, the second label, and the buffer; and stage C further comprises:

calculating the differences between: %-activated platelets in second PCH sample and %-activated platelets in second PC sample, and comparing said differences for said second PIH and second PI samples, and for said second PCH and said second PC sample, wherein HIT is further diagnosed in the patient's sample when said difference for said second PIH and second PI samples is similar to said difference for said second NCH and said second NC sample.

The incubation in Stage A may be for about an hour and the incubation in Stage B may be for about 15 minutes.

The concentration of heparin in the first PIH and NCH samples is typically between 0.1 and 0.5 IU/mL.

Preferably, the concentration of heparin is about 0.3 IU/mL.

Preferably, the buffer is calcium and magnesium-free PBS.

In some embodiments, the first label is a a fluorescence labeled monoclonal antibody anti-platelet CD41a.

According to another aspect, a method comprising at least one of the following methods is provided for use in determining the platelet-related condition of a patient:

diagnosing HIT as described above;

APS diagnosing in the patient's serum or plasma sample, the APS diagnosing comprising:

preparing a platelet suspension from a blood sample from an individual not having APS;

treating the platelets from the individual not having APS, by exposing membrane phospholipids in the platelets;

incubating the patient's sample with said treated platelets to obtain a suspension of patient's sample with exposed normal platelets (SPEP);

purifying unlabeled annexin;

adding an excess of FITC to the purified annexin at pH=9.2 to form a highly labeled annexin;

purifying the highly labeled annexin;

incubating the purified highly labeled annexin with the said SPEP;

determining, in a subsample of SPEP incubated with annexin, an amount of highly labeled annexin bound to platelets in the subsample, whereby a low ratio indicates APS in said sample;

ITP (immune thrombocytopenia) diagnosing the sample, the ITP diagnosing comprising:

preparing either:

A) patient's antibodies:

covering a first surface with MoAb anti-platelet specific receptors; subsequently incubating the covered first surface with lysate from normal platelets;

subsequently incubating the covered first surface and lysate with an aliquot of the patient's sample;

subsequently adding a secondary fluorescence-labeled Ab against human immunoglobulin, or:

B) patient's antibody-platelet specific antigen complex:

covering a first surface with MoAb anti-platelet specific receptors; subsequently incubating the covered first surface with lysate from the patient's platelets;

subsequently adding a secondary fluorescence-labeled Ab against human immunoglobulin;

C) preparing a reference:

covering a second surface with MoAb anti-platelet specific receptors; subsequently incubating the covered second surface with lysate from normal platelets;

subsequently incubating the covered second surface and lysate with normal serum or plasma;

subsequently adding a secondary fluorescence-labeled Ab against human immunoglobulin, and D) comparing a first quantification of secondary-labeled antibody adsorbed on said incubated first surface to second quantification of secondary-labeled antibody adsorbed on said incubated second surface, wherein a first quantity substantially more than the second quantity indicates ITP in said sample;

platelet function diagnosing the sample, the method comprising:

A) assessing platelet stimulation:

1) simultaneously incubating platelet-containing samples of the patient and of normal individuals, each with two labeled MoAb against platelet glycoproteins, to provide labeled platelets of patient and platelets of normal individuals, first said labeled MoAb having a measurement in a first band and second said labeled MoAb having measurement in a second band;

2) subsequently adding to said samples each either ADP or TRAP to provide stimulated labeled platelets of patient and of normal individuals;

3) subsequently identifying labeled platelets in said samples by measuring in said first band or in said second band;

4) subsequently measuring said identified labeled platelets of patient and said identified labeled platelets of normal individuals, wherein the measurement of said identified labeled platelets is in said second band when the labeled platelets are identified by the first band, and is in said first band when the labeled platelets are identified by the second band;

5) wherein the measurement of said identified labeled platelets of said patient equal to or more than the mean+2 standard deviations (2SD) said measurement of said labeled platelets of normal individuals indicates platelet activation in said sample of patient;

B) assessing platelet procoagulation:

1) simultaneously incubating platelet-containing samples of the patient and of a normal individual, each with labeled MoAb against platelet glycoproteins, and annexin V;

2) subsequently incubating said samples each with platelet ionophores;

3) subsequently identifying a similar amount of labeled platelets in said samples by measuring labeled MoAb against platelet glycoproteins;

4) subsequently measuring fluorescence of annexin V on said similar amounts of platelets;

5) wherein an annexin V fluorescence of the patient's platelets equal to or more than the mean+2 standard deviations (2SD) the Annexin V fluorescence of the normal individual's platelets indicates platelet procoagulation in said sample of patient;

Bernard-Soulier syndrome diagnosing in said sample, the diagnosing comprising:

1) simultaneously incubating platelet-containing samples of the patient and of normal individuals, each with a-first labeled MoAb against platelet specific glycoproteins excluding CD 42 (GPIb-IX-V complex), and with a second labeled MoAb against CD42;

2) subsequently identifying labeled platelets in said samples by measuring first labeled MoAb,
   subsequently measuring said second MoAb from said identified labeled platelets of patient and said second MoAb from said identified labeled platelets of normal individuals, wherein the measurement of said second MoAb binding by said identified labeled platelets of patient's is significantly less than said identified labeled platelets of normal individuals, indicating Bernard-Soulier syndrome, and 3) wherein the measurement of said second MoAb of said identified labeled platelets of patient's relative is less than normal but greater than patient, indicate a carrier state;

Glanzmann thrombasthenia syndrome diagnosing in said sample, the diagnosing comprising:

1) simultaneously incubating platelet-containing samples of the patient and of normal individuals, each with labeled MoAb against platelet glycoproteins excluding CD41a, and with MoAb against CD41a;

2) subsequently identifying labeled platelets in said samples by measuring MoAb against platelet glycoproteins excluding CD41a, 3) subsequently measuring MoAb against CD41a of said identified labeled platelets of patient and MoAb against CD41a of said identified labeled platelets of normal individuals, 4) wherein a first measurement of MoAb against CD41a in patient's sample is equal or less than the mean−2 standard deviations (2SD) measurement of MoAb against CD41a binding to said normal individual's platelets, indicates Glanzmann thrombasthenia syndrome in said sample of patient, and a first measurement in between a measurement of a sample from an individual having the syndrome, and a measurement of a sample of a normal individual indicates a Glanzmann thrombasthenia carrier;

drug inhibitory effect diagnosing of said sample, the diagnosing comprising:

A)

1) simultaneously incubating platelet-containing samples of the patient and of normal individuals, each with labeled MoAb against platelet glycoproteins CD41a or CD61, CD62p and activated CD41a;
2) subsequently incubating said samples with a stimulator selected from one or more of the group comprising: ADP, arachidonic acid and TRAP;
3) identifying labeled platelets in said samples by measuring MoAb against platelet glycoproteins CD41a;
4) subsequently measuring MoAb against platelet glycoproteins CD62p and activated CD41a of said identified labeled platelets of patient and said identified labeled platelets of normal individuals,
5) wherein either measurement of MoAb against platelet glycoproteins CD62p of patient equal or less than the mean−2 standard deviations (2SD) measurement of MoAb against platelet glycoproteins CD62p of said normal individuals, or measurement of MoAb against platelet glycoproteins activated CD41a of patient equal or less than the mean−2 standard deviations (2SD) measurement of MoAb against platelet glycoproteins activated CD41a of said normal individuals indicates a drug inhibitory effect in said sample of patient;
B) determining assessing platelet procoagulation as in platelet function diagnosing, wherein the platelets are stimulated with calcium ionophore then incubated with labeled annexin A5;
determining circulating platelet or platelet-related particles activation labels as indicators of ongoing, real-time in vivo, prothrombotic activity, comprising:
1) incubating aliquots of patient's and normal control blood or PRP sample with one or more of fluorescence-labeled;
receptor specific MoAb for immune-detection of platelets and platelet-related particles, the receptor specific MoAb excluding anti-activated CD41a (GPIIb/IIIA) antibody, anti-P-selectin CD62p antibody;
anti-activated CD41a (GPIIb/IIIA) antibody; anti-P-selectin CD62p antibody;
Annexin A5 protein against platelet anionic-phospholipids for detection of platelet procoagulant activity;
2) following incubation for 15-30 minute at room temperature, diluting said samples with buffer and analyzing,
wherein signal level of patient's sample equal or greater to mean of normal+2 standard deviation indicates activation of circulation platelets or platelet-related particles.
According to yet another aspect, a system comprising kits for performing the HIT diagnosis described above is provided.

According to another aspect, a system comprising kits for performing one or more of the diagnoses described above is provided.

BRIEF DESCRIPTION OF THE FIGURES

For a better understanding of the invention and to show how it may be carried into effect for the diagnosis of platelet-associated disorders, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice.

In the accompanying drawings:

Figure 1:
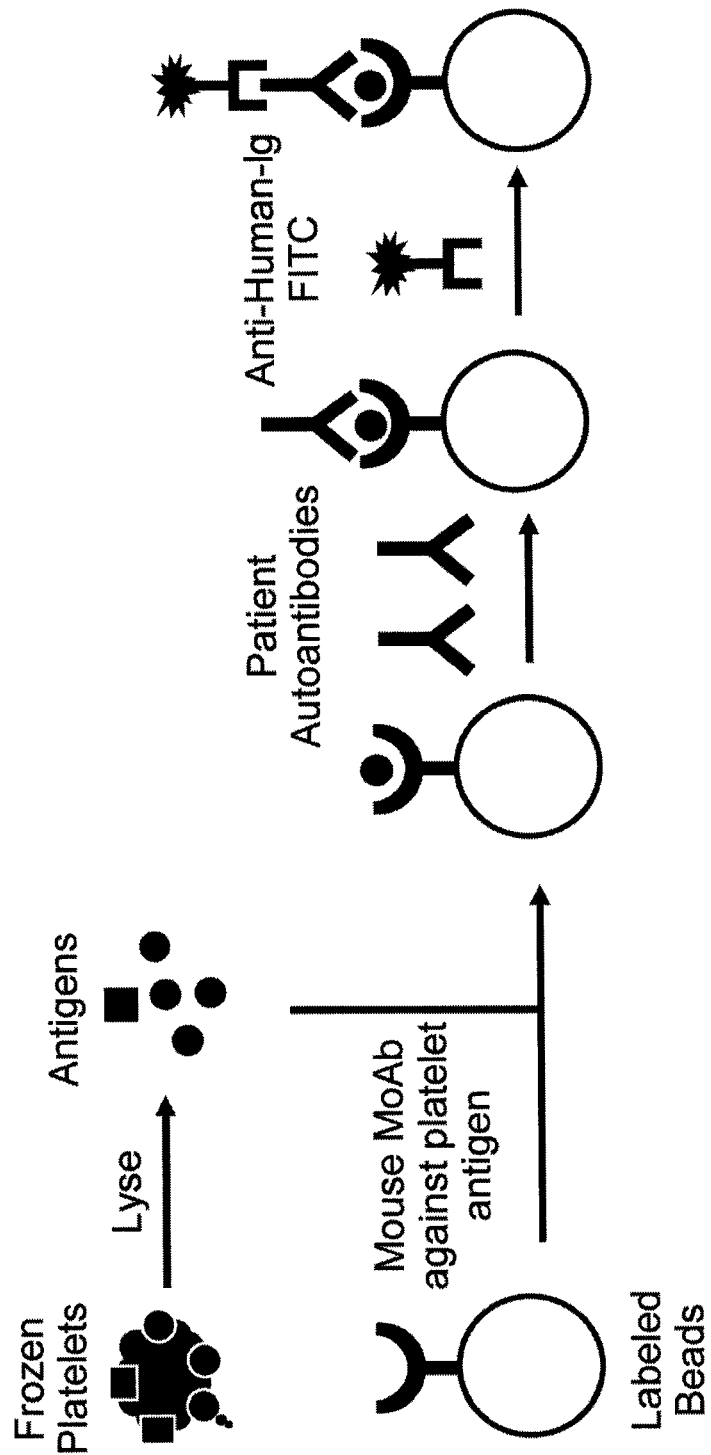

FIG. 1. Process for determination of circulating auto-antibodies and allo-antibodies against platelet-specific receptors. Polystyrene microbeads are coated with monoclonal antibodies directed against platelet-specific glycoproteins. Then the specific glycoproteins are extracted from normal human platelets and immobilized on the microbeads' surface. Patient serum or plasma is incubated with the glycoprotein coated beads. Then the beads are washed, incubated with secondary fluorescence-labeled anti human immunoglobulin, and analyzed for the level of antibody binding, as compared to normal control sample.

Figure 2:
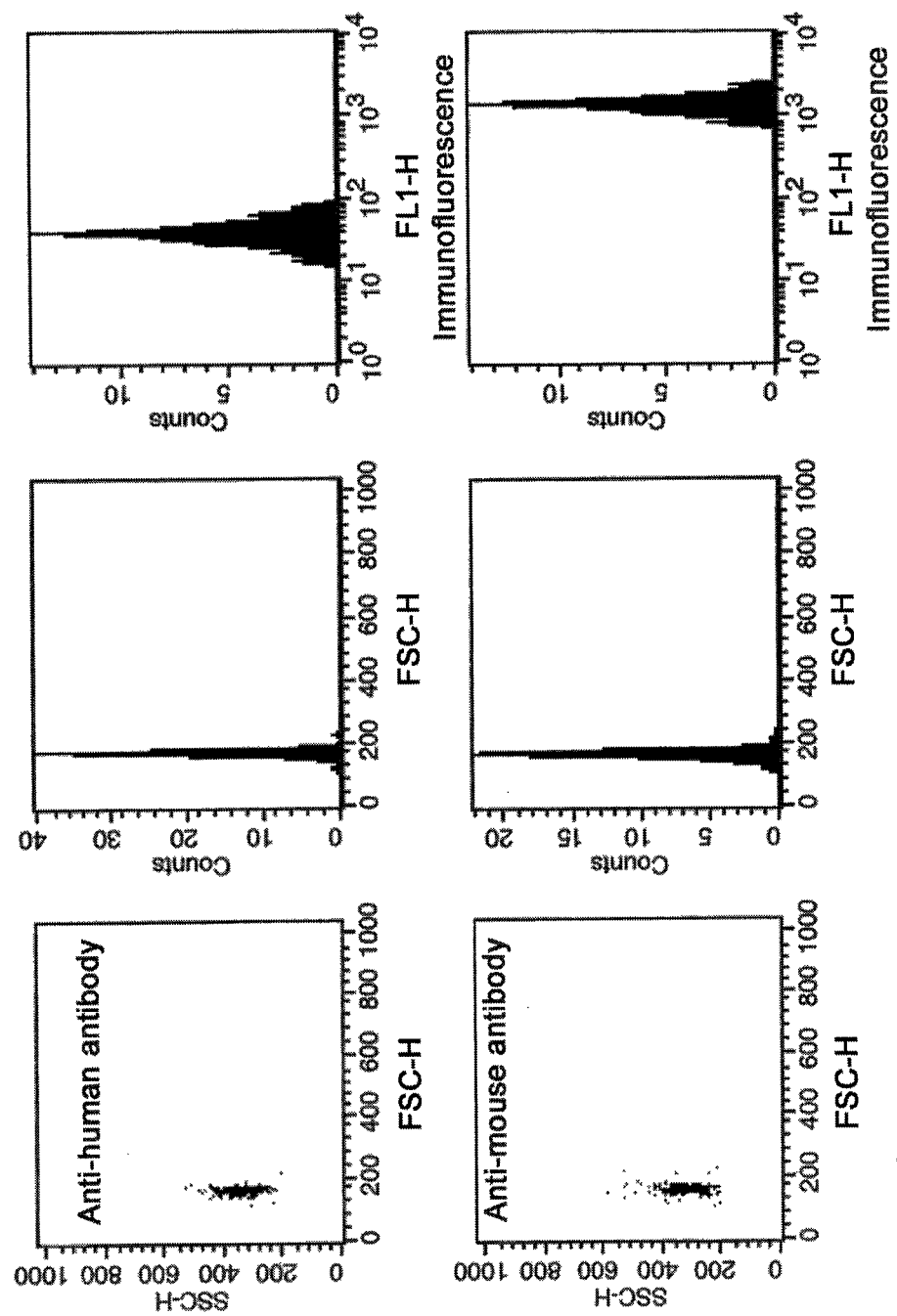

FIG. 2. The binding of mouse monoclonal antibodies against platelet-specific glycoproteins to the polystyrene microbeads, mentioned above. In this control assay high fluorescence level is demonstrated with the anti-mouse antibody, compared to control sample incubation with an anti-human antibody.

Figure 3:
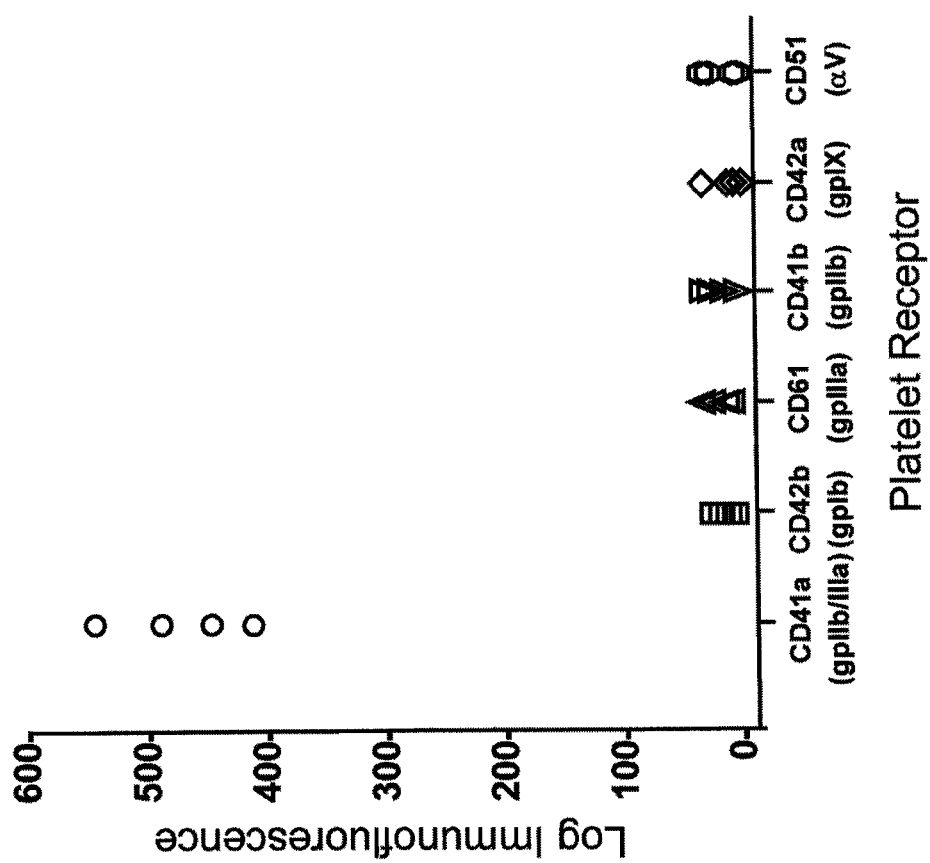

FIG. 3. Example results of testing an ITP patient. The patient's serum or plasma are reacting with platelet CD41a (GPIIb/IIIa) immobilized on the microbeads. The specificity is high, without antibody reaction with other platelet receptor glycoproteins.

Figure 4:
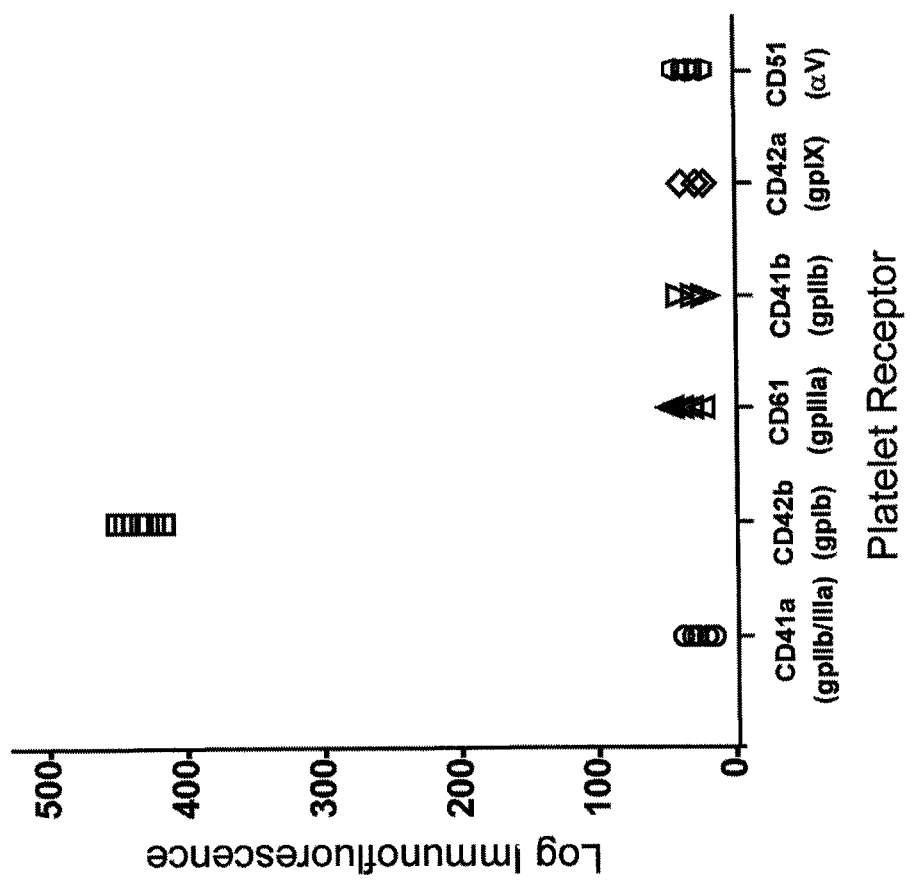

FIG. 4. Example results of serum or plasma of a different patient with ITP reacting with platelet CD42b (GPIb) immobilized on microbeads. The specificity is high, without antibody reaction with other platelet glycoproteins.

Figure 5:
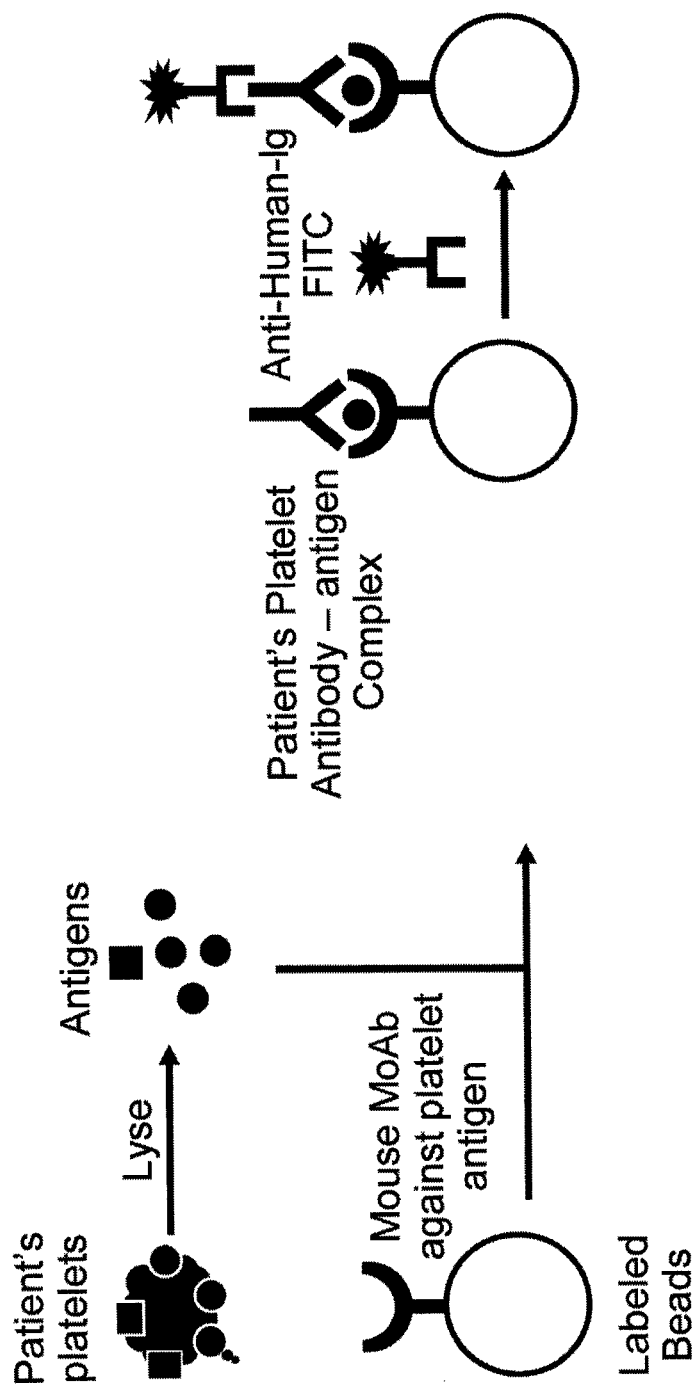

FIG. 5. A schematic drawing of a process for determination of platelet-bound auto-antibodies and allo-antibodies, against platelet-specific receptors. Microbeads are coated with monoclonal antibodies directed against platelet-specific glycoproteins. The in vivo formed antibody-platelet-antigen complexes are then extracted from the patient's platelets and immobilized on the microbeads' surface. The beads are then washed, incubated with secondary fluorescence-labeled anti-human immunoglobulin, and analyzed for the level of human antibody binding, as compared to normal control platelet sample.

Figure 6:
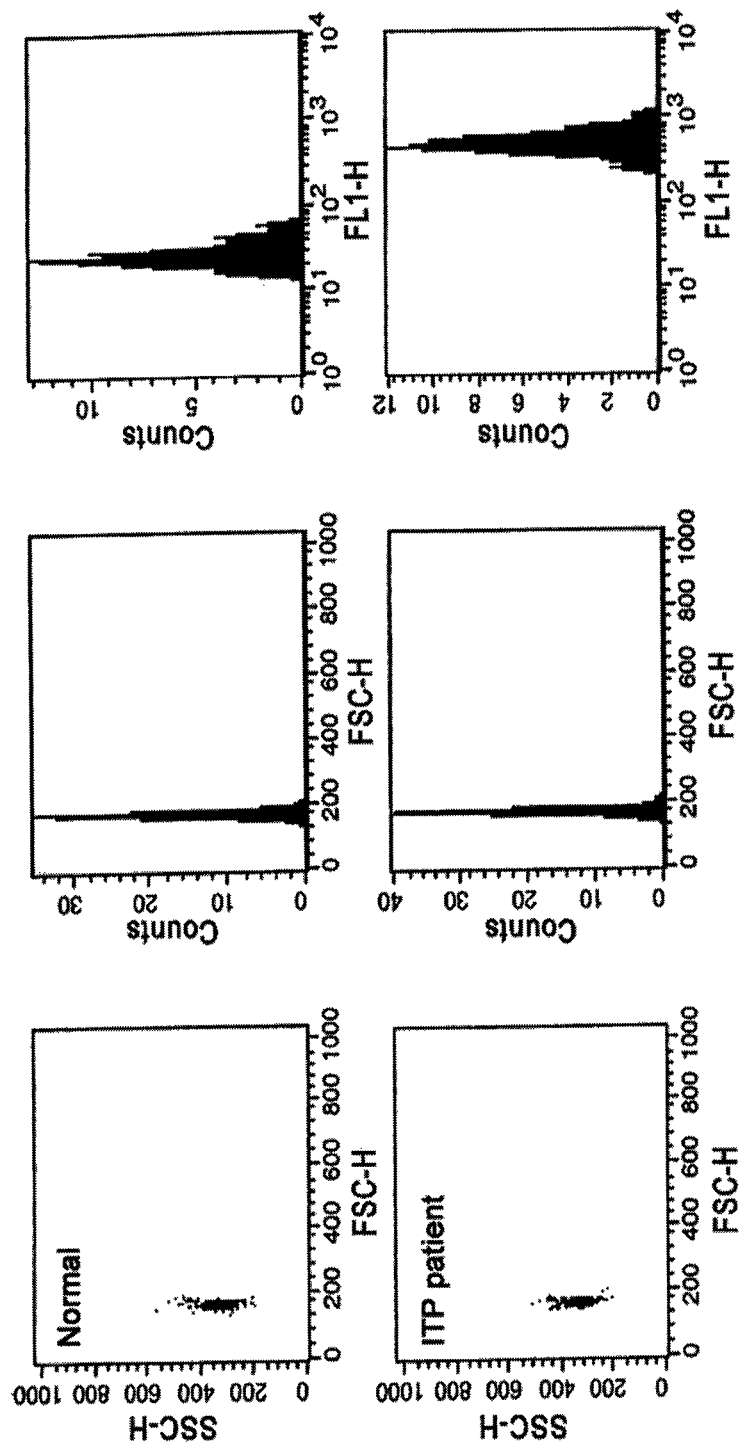

FIG. 6. Analysis of in vivo formed antibody-antigen complex on platelets from patient with ITP, showing auto-antibodies bound to the platelet CD41a (GPIIb/IIIa) complex. A high level of antibody binding is demonstrated compared to normal control sample. FL1 Denotes Fluorescence 1.

Figure 7:
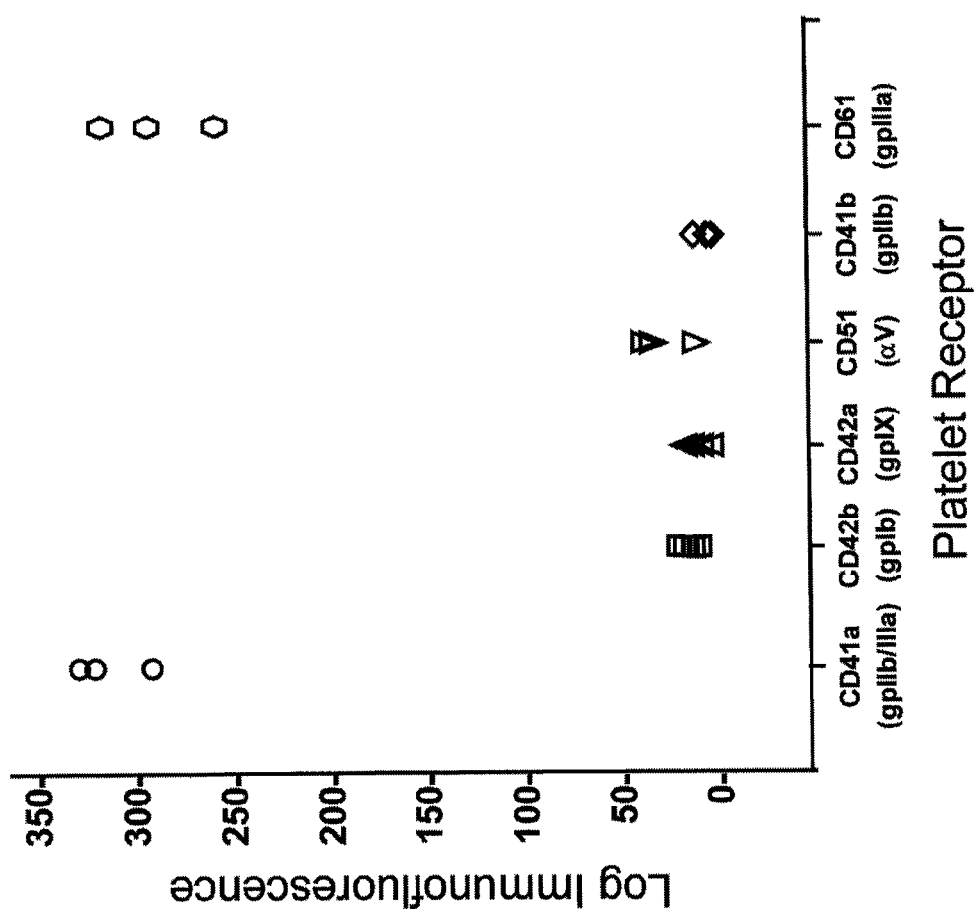

FIG. 7. Analysis of circulating allo-antibodies against a platelet-specific receptor. Serum or plasma from patient with post-transfusion purpura-PTP reacting with both platelet CD41a (GPIIb/IIIa) complex, and CD61 (GPIIIa) glycoprotein subunit, which is typical of PTP. The specificity is high without antibody reaction with other platelet glycoproteins.

Figure 8:
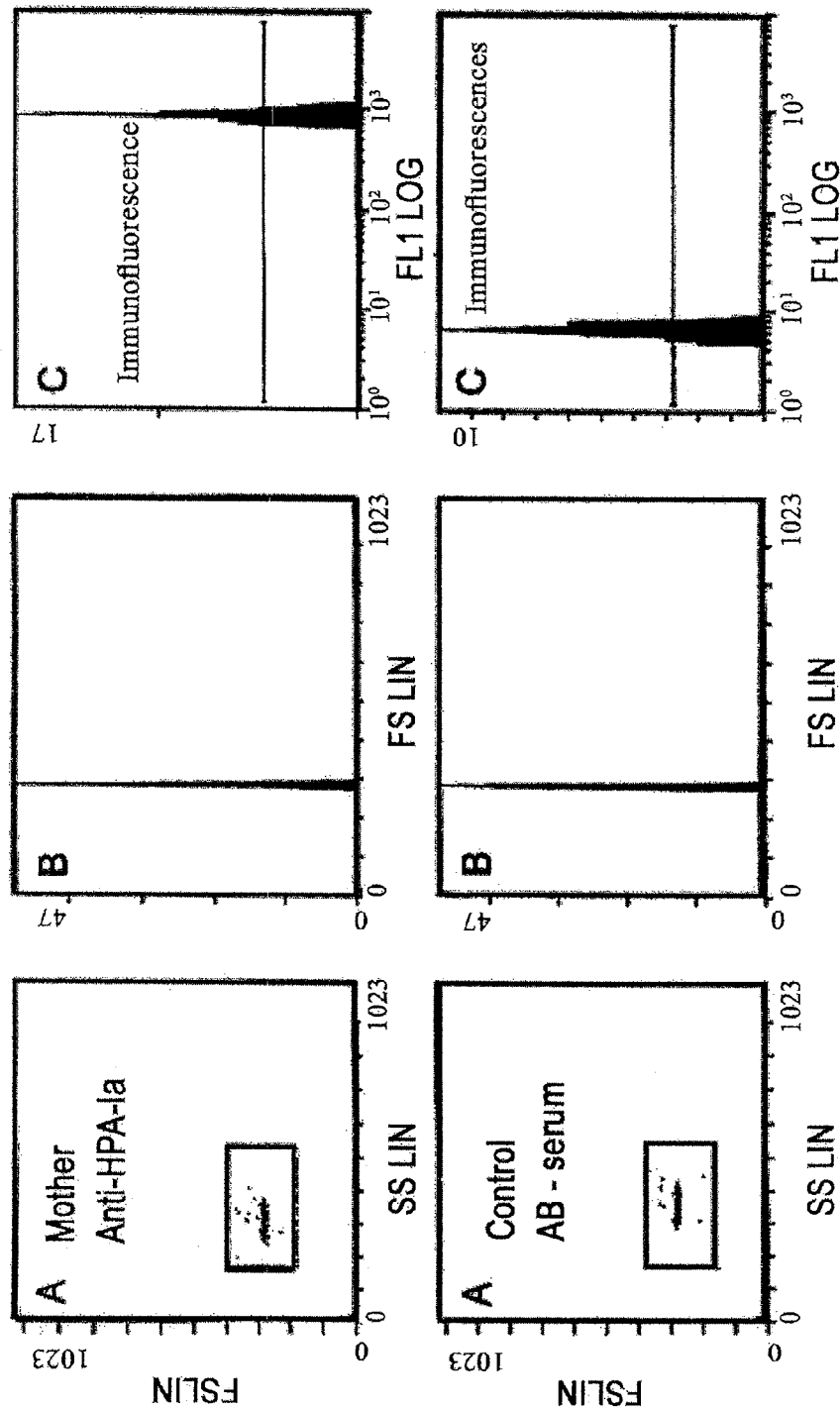

FIG. 8. Analysis of circulating allo-antibodies in Neonatal-Alloimmune Thrombocytopenia-NAIT: A pregnant woman with NAIT demonstrating reaction of her serum or plasma against child or husband human-platelet-antigen 1a (HPA-1a) allele. The pregnant women is homozygote for the HPA-1b allele. A very high immunofluorescence signal is demonstrated compared to normal control.

Figure 9:
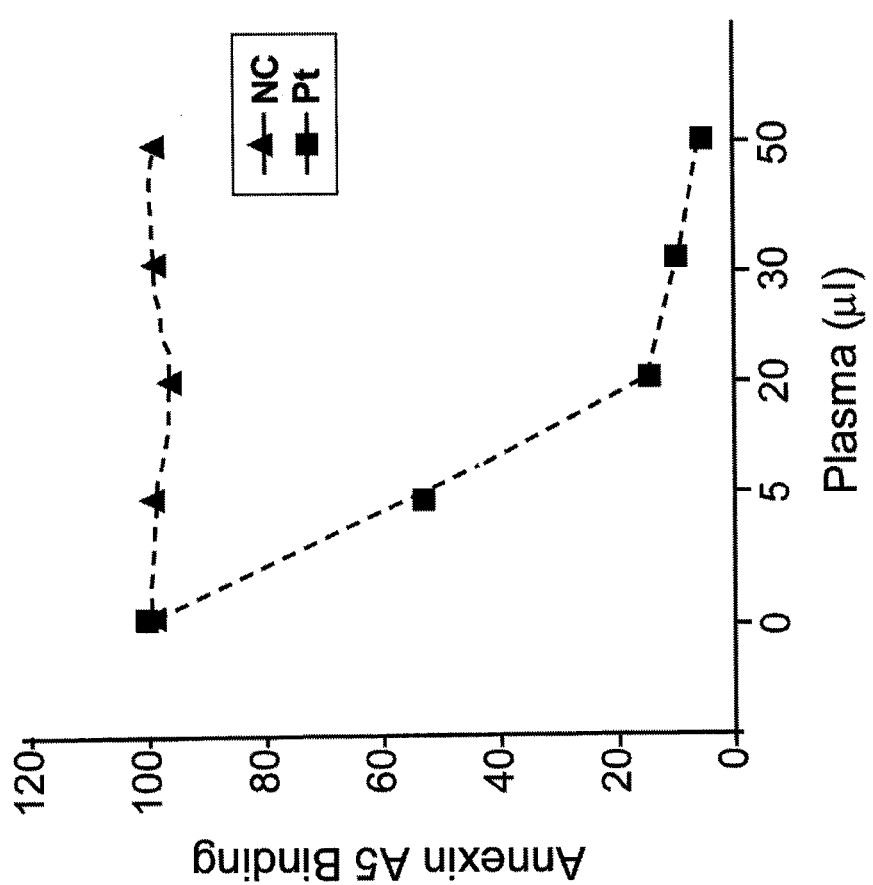

FIG. 9 demonstrates the inhibitory effect of serum or plasma from patient with anti-phospholipid-antibody syndrome—APS (Pt) on the binding of Annexin A5 to platelet membrane phospholipids. No inhibitory effect is observed with plasma from healthy control (NC). Assay is performed by flow cytometry.

Figure 10:
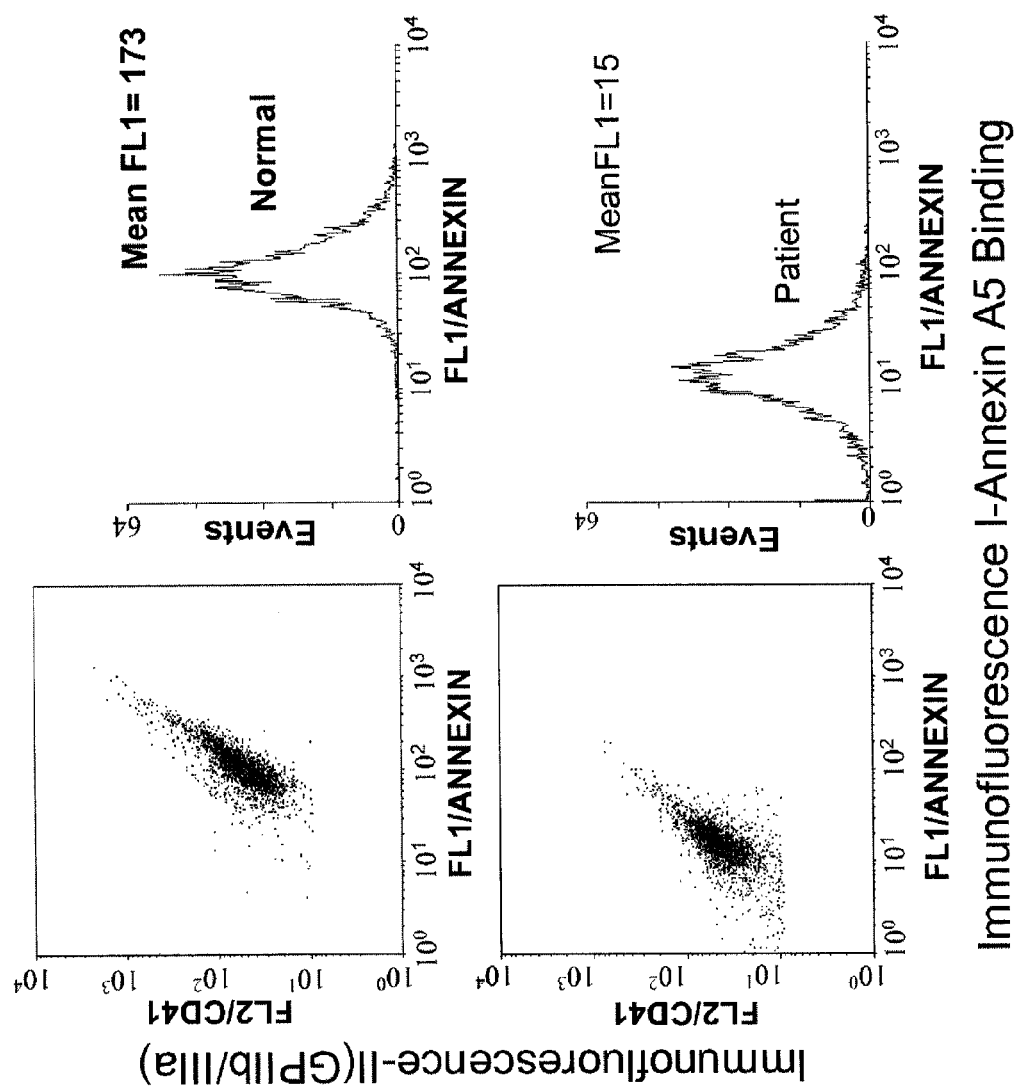

FIG. 10 demonstrates the flow cytometric testing of serum or plasma from patient with APS. Significant reduction in the binding of Annexin A5 to platelet phospholipids is observed with patient's sample compared to normal control, consistent with the diagnosis of APS.

Figure 11:
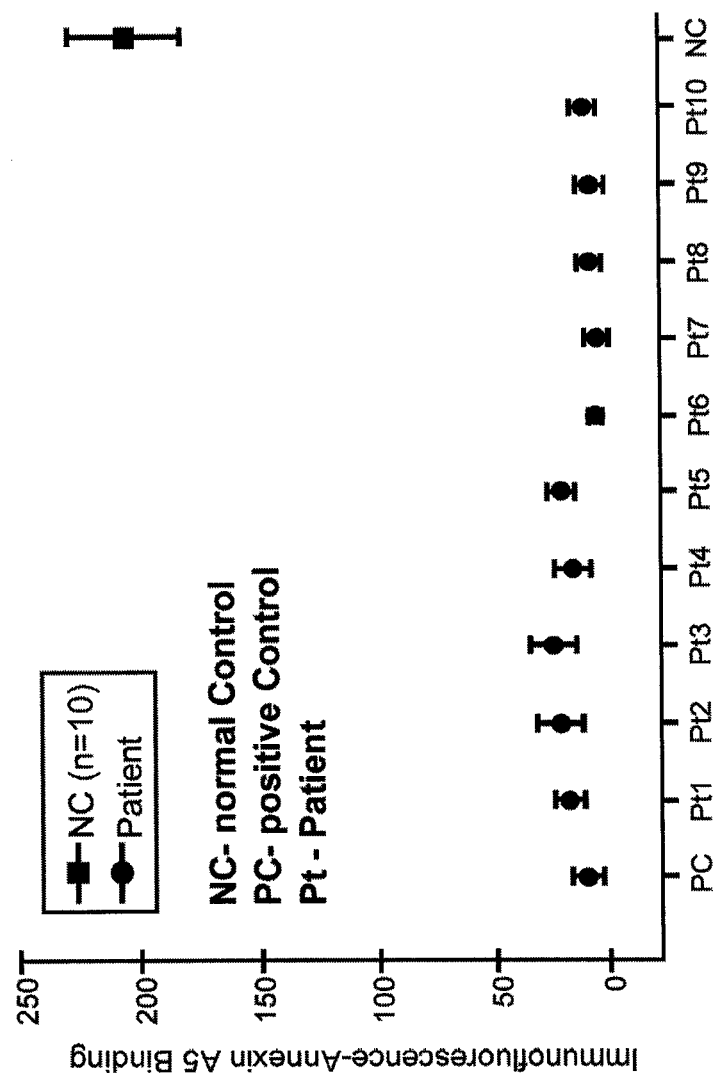

FIG. 11 depicts reduced Annexin A5 binding to platelet phospholipids in APS patients (Pt), compared to normal controls (NC). High resolution between patients and healthy controls is shown.

Figure 12:
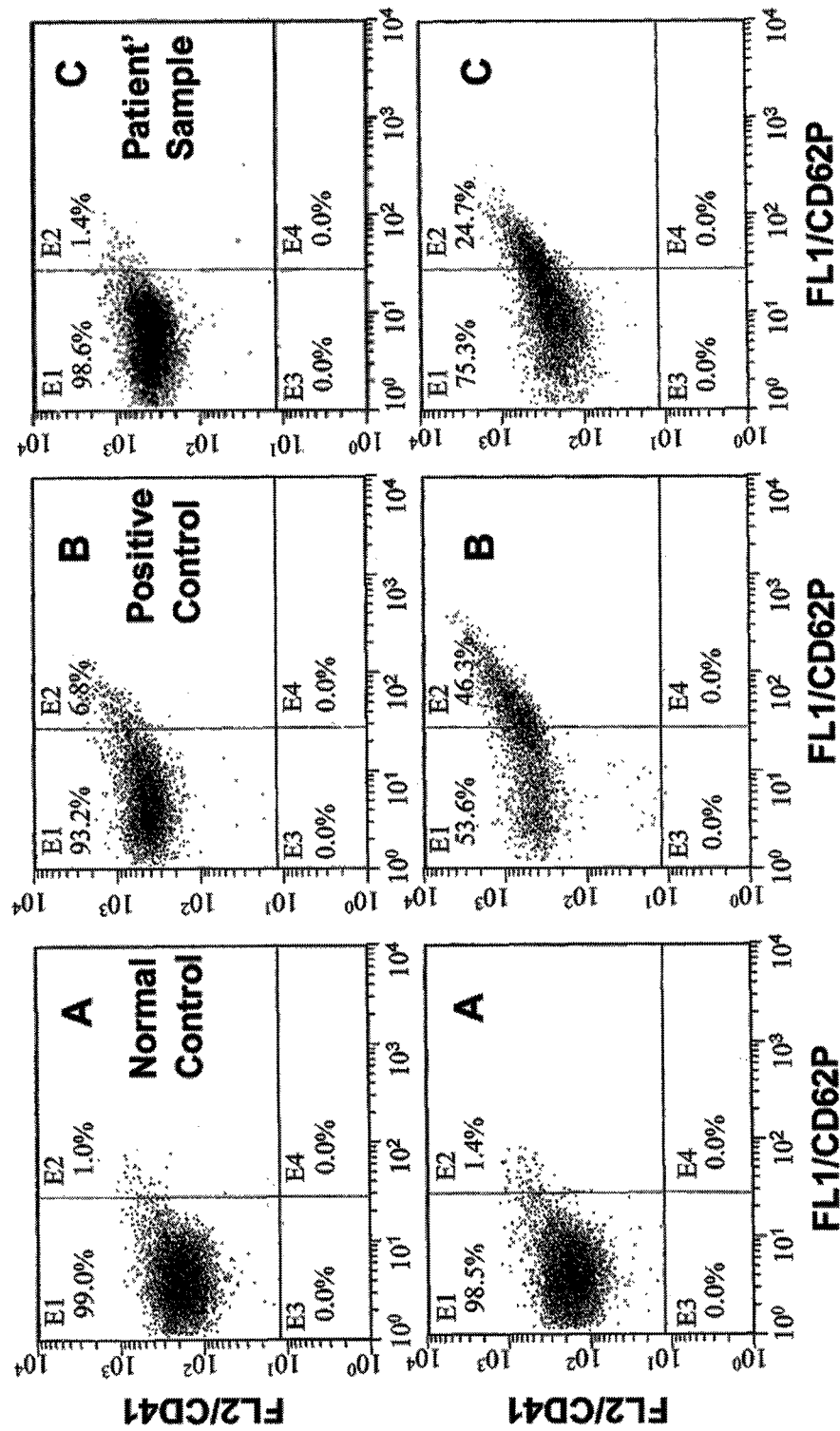

FIG. 12 shows testing of sample from patient with heparin-induced thrombocytopenia (HIT). The serum/plasma sample was incubated with normal platelets in the absence (0.0) (upper panels) and the presence (0.3 U/mL) (lower panels) of heparin.

A-normal control; B-positive control—HIT patient; C-patient clinically suspected for HIT. The patient's sample (C) shows significant increase in activated platelets, from 1.4% without, to 24.7% with heparin. A high percentage of activated platelets (upper-right quadrants of the boxes) is demonstrated in both positive control and tested patient, compared to normal control.

Figure 13:
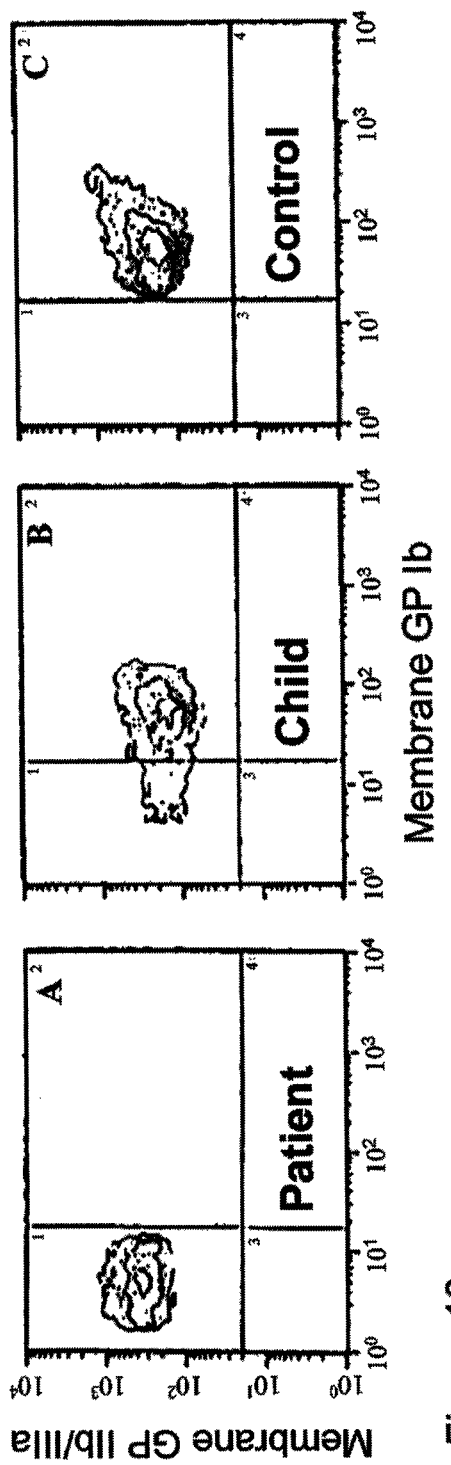

FIG. 13 demonstrates the diagnosis of Bernard-Soulier syndrome by Flow Cytometry. The Patient's blood platelets show normal expression of GPIIb/IIIa but deficient expression of GPIb, which is characteristic of Bernard-Soulier Disease. A child of the patient shows intermediate expression of GPIb, indicating a carrier state.

Figure 14:
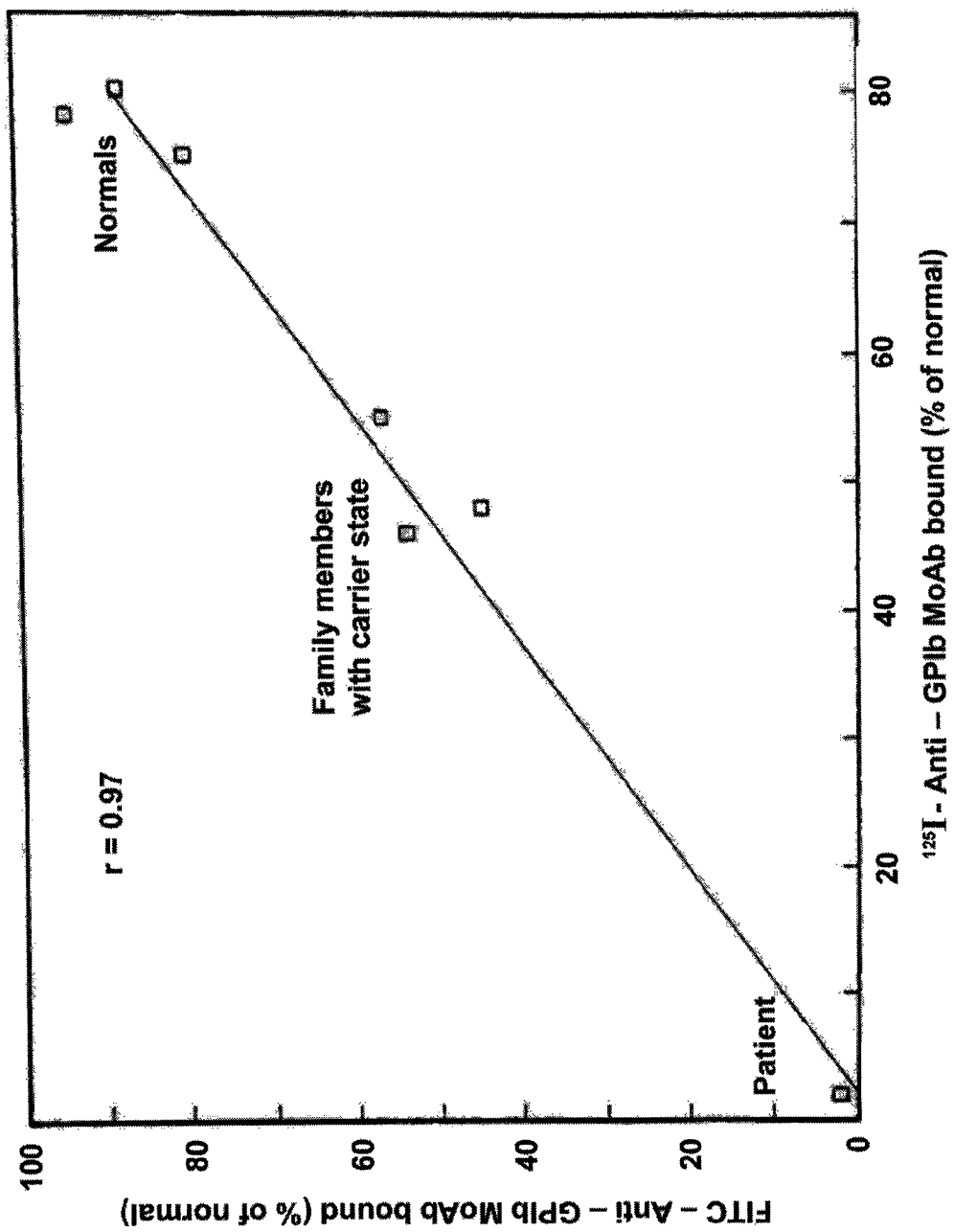

FIG. 14 demonstrates the accuracy of the flow cytometric determination of Bernard-Soulier Syndrome, with high correlation between the binding of FITC-labeled and $^{125}$I-labeled anti-GPIb antibody to platelets. Three groups are identified, the patient with severe deficiency of GPIb (lower-left corner), three relatives with intermediate expression of GPIb (middle of the graph) representing a carrier state, and normal controls (upper-right) showing high expression of GPIb.

Figure 15:
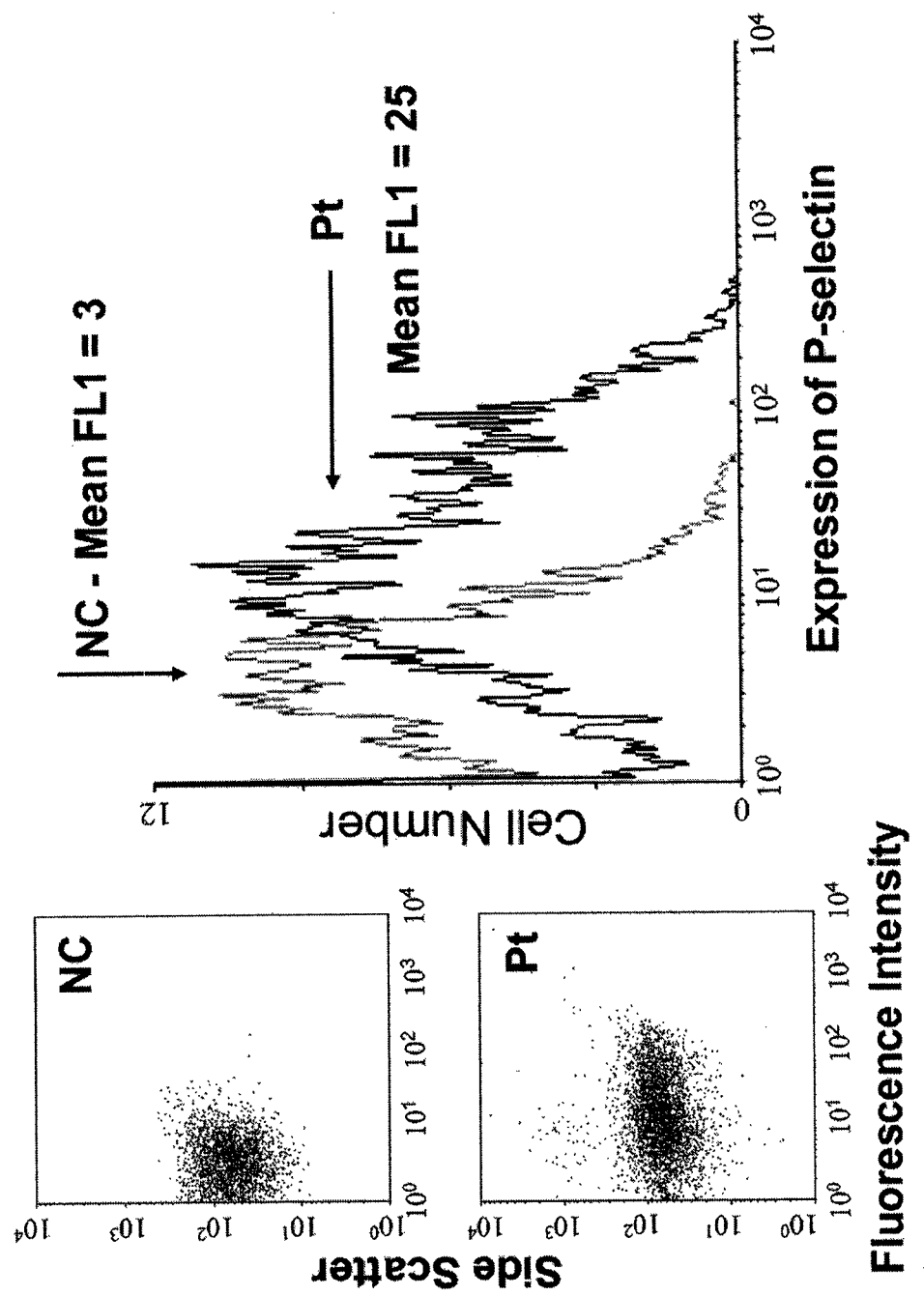

FIG. 15 demonstrates the increased expression of p-selectin (CD62p) by circulating platelets, indicating in vivo activation state in patient at risk for thrombosis (Pt), as compared to healthy normal control (NC). P-selectin is an α-granule glycoprotein expressed on platelets following activation and release reaction. Thus, it is a marker for in vivo prothrombotic activity.

Figure 16:
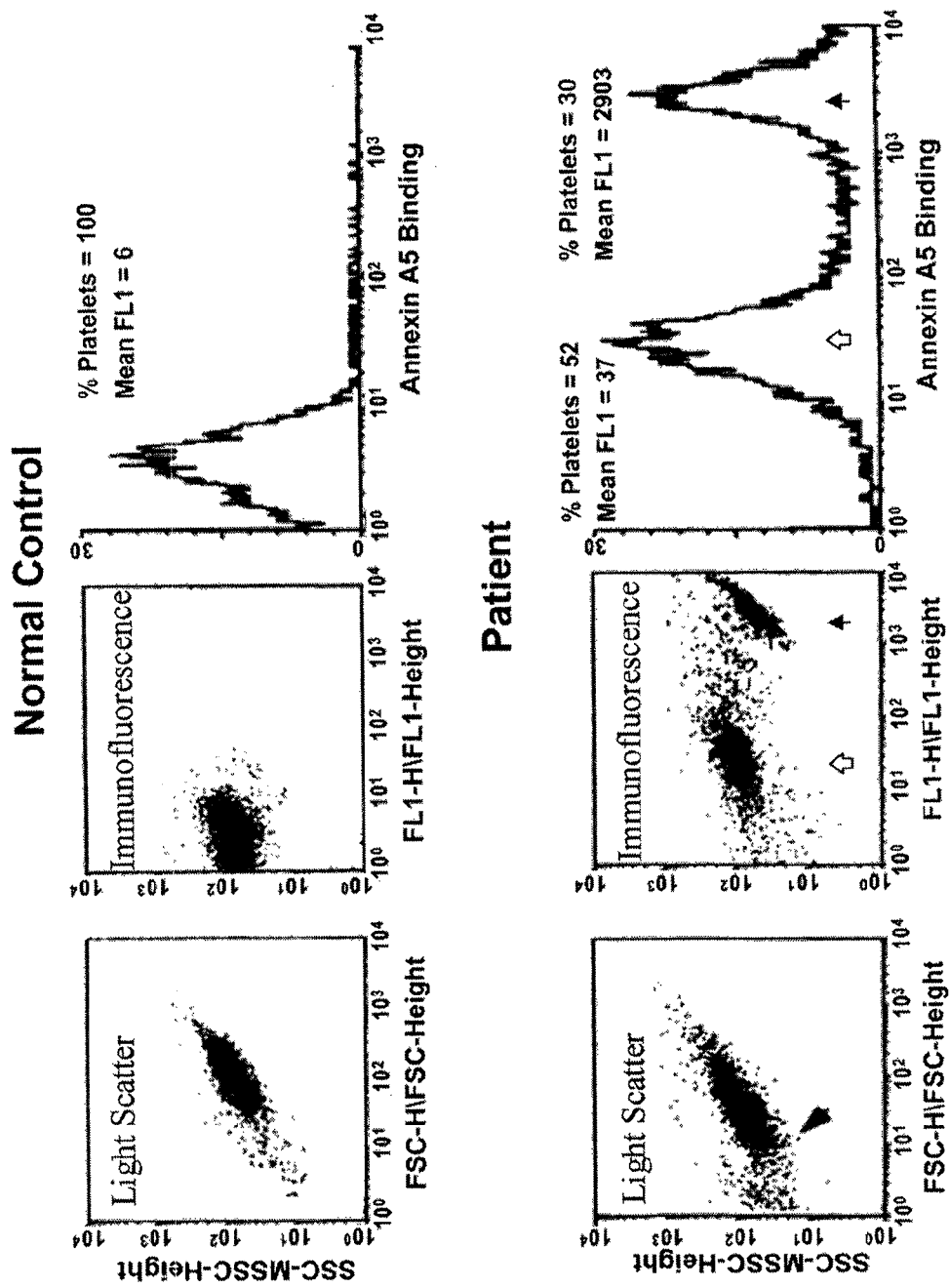

FIG. 16 demonstrates the expression of platelet procoagulant activity as detected by Annexin A5 binding, in patient at high-risk for thrombosis. Both activated platelet population (open arrow), and highly-activated platelet particles (black arrow head) are shown, indicating high in vivo platelet activation state consistent with ongoing prothrombotic activity in the patient's blood.

DESCRIPTION OF THE PREFERRED EMBODIMENTS

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The terms "comprises", "comprising", "includes", "including", and "having" together with their conjugates mean "including but not limited to".

The term "consisting of" has the same meaning as "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

In discussion of the various figures described herein below, like numbers refer to like parts. The drawings are generally not to scale. For clarity, non-essential elements were omitted from some of the drawings.

Systems, kits and methods described hereinbelow serve to diagnose medical conditions related to blood platelets. According to one aspect, a system comprising a testing panel is provided, that may allow performing several assays. However, all these assays are concentrating on the subject of testing coagulation disorders related to blood platelets. The overall purpose of the assays is to enable the identification of patients with tendency for either bleeding or thrombosis, and to allow a rationally-based appropriate medical intervention.

It is important to note that according to one aspect, the system represents one unit, which is designed to provide a clinical answer to platelet conditions that may arise from various causes, thus requiring more than one test to arrive to the correct diagnosis. For example, a state of low platelet count-thrombocytopenia may require assay for immune thrombocytopenia—IT/ITP, APS (anti-phospholipid syndrome) that may be complicated by thrombocytopenia, heparin-induced thrombocytopenia-HIT if the patient is also exposed to heparin, and Bernard-Soulier disease—a platelet function defect that is also associated with thrombocytopenia. Thus, by ruling out confounding conditions, the correct diagnoses can be made, saving the patient unnecessary or inappropriate therapy or surgical procedures, as happens sometimes with Benard-Soulier disease patients for example, who are wrongly diagnosed with ITP and referred for splenectomy. This is because the lack of appropriate laboratory tests, such as described below, to rule out ITP for example, or lack of appropriate facilities to carry out some of the tests, for example non-hematologic laboratories are typically not equipped to perform many of the currently known tests.

According to one aspect, a system comprising both a dedicated instrument and a panel of reagents is provided, the latter in the form of specific diagnostic kits. An exemplary flow-cytometer is described below. Alternatively, some commercially available instruments may be adjusted—such as for example by modification of software—to perform the desired tests.

Test methods based on detecting platelet antibody-antigen reactions are provided. The methods may all be performed using standard fluorescence flow-cytometry, which is quite common. However, in some embodiments, other methodologies for detecting such reactions may be used. One methodology is chemiluminescence, but also solid-phase type assay, ELISA, gel-particle agglutination assay and others may be suitable.

Test method embodiments include sample preparation, using fresh samples of blood or platelets, but alternatively, all the assays can be performed on fixed preparations.

Typically, all the diagnosis kits and methods described below make use of a particular antibody—anti-CD41a—as the best probe for general detection of the platelets. However, other probes for detecting platelets such as anti-CD42 or anti-CD61 may be used instead or in addition, according to the particular test.

Following are descriptions of exemplary methods and kits for diagnosis of platelet—related conditions.

1. Platelet Immunity—IT or ITP (Platelet Immune thrombocytopenia)

In order to overcome the limitations of currently available methods, and to facilitate the diagnosis of IT, we developed a reliable, feasible, rapid, sensitive and specific flow cytometric method using a microbead technique for the determination of circulating autoantibodies reactive with or directed against platelet-specific glycoprotein receptors. The method is applicable for both Autoimmune and Alloimmune clinical disorders.

In summary, this method allows the direct and positive identification of patients with IT—the discrimination of IT from other confounding conditions causing thrombocytopenia such as decreased platelet production and APS (which may be associated with thrombocytopenia but with tendency for thrombosis rather than bleeding as in IT). The direct and reliable analysis will enable the physician to directly confirm the diagnosis and provide the IT patient with the appropriate medical therapy for his/her condition.

Technology in General:

Methods and kits have been developed for testing platelet-antigen-specific auto-antibodies and allo-antibodies, in patient's plasma, and/or platelet-specific receptor:antibody complexes formed in vivo, using fluorescence microbead assay.

The method is applicable for any technique using fluorescent microbeads, either by flow cytometry or by direct fluorometric micro-well reading. The method can also be employed using chemiluminescent microparticles, or color development (as in ELISA) or gel-particle agglutination techniques (for example gel-particles coated with antigen and agglutinated in the presence of an antibody, as is commonly used in blood banking), as well as immobilization of the antibodies or platelet:antibody complexes on solid surfaces.

The method is suitable for testing a single sample as well as multiple samples as needed, and for detecting antibody reactions with a single platelet glycoprotein or by multiplex analysis detecting antibody interaction with multiple platelet glycoproteins.

Products of the present technology may be provided to the clinical laboratories in the form of diagnostic kits, optionally together with instructions—protocol—for performing the test, to assist with the diagnosis of clinically important disorders.

Process 1:

According to some embodiments, a kit and a method for the determination of circulating auto-antibodies against platelet-specific receptors in autoimmune thrombocytopenia (ITP) are provided. The process is based on the detection of a patient's auto-antibodies reacting with platelet-specific glycoproteins immobilized (adhered) on plastic (or any suitable polymer) microbeads surface. The microbeads are first coated with monoclonal antibodies directed against platelet-specific glycoproteins, then incubated with the extracted platelet glycoproteins—as fully specified below.

The method obviates using patient platelets, which may be difficult to obtain in severe thrombocytopenia.

Target platelet glycoproteins include but are not restricted to CD41a (GPIIb/IIIa), CD42b (GPIb), CD61 (GPIIIa), CD41b (GPIIb), CD42a (GPIX), and CD51 (aV).

Materials and Methods

Polystyrene beads (15 μm diameter; Polysciences, Inc. 400 Valley Road, Warrington, Pa. 18976, USA) were coated overnight at 4° C. and pH=9.2 buffer by gentle mixing with monoclonal antibody against GPIIb/IIIa (20 μg/mL) final concentration (P2 clone, Immunotech, West Brook, Me., USA). The beads were then washed with PBS buffer.

Normal platelet samples were solubilized with 0.5% Triton X-100 and centrifuged for 5 min at 1200×g. All procedures were carried out at room temperature.

For the regular assay, 2500 antibody coated beads were incubated with the platelet lysate for 2 h, washed and stored at 4° C. until assay.

For the assay, coated beads are incubated with patient's serum or plasma for hours with gentle rocking at room temperature, then washed in PBS+2.5% BSA and incubated for 1 h with fluorescein labeled polyclonal goat antihuman immunoglobulin antibody (20 μg/mL); Vector Laboratories, Inc., Burlingame, Calif., USA).

Following incubation, the bead suspension is diluted with PBS and analyzed by flow cytometry (FIGS. 1-4, 7).

Flow cytometric assay: Beads are initially identified and electronically gated by light scatter. One thousand events were collected for each sample. Non-specific antibody binding was measured using goat anti-rabbit antibody (Vector) with a similar fluorescein: protein ratio. The negative controls consist of normal serum obtained from healthy individuals. Mean fluorescence of the tested beads was determined using the standard flow cytometer software. The time required for the entire assay using the coated microbeads is approximately 4 h (Compare to research MIPA method usually requiring days to complete). Up to 12 assays could be conveniently run at the same time.

Statistical analysis: Comparison between results of tests performed on samples of patients and those performed on samples from normal individuals was performed using the non-parametric Kruskal-Wallis test. Individual fluorescence levels and fluorescence of three normal controls were simultaneously tested. A fluorescence of patient sample equal to or more than the mean fluorescence of normal samples+2 standard deviations (2SD) was considered positive. Once the normal range has been established, just one normal sample can be run for control.

Eighteen patients with clinical diagnosis of ITP were studied. Fourteen patients demonstrated auto-antibodies against CD41a (mean fluorescence 320±137 vs. 7±2 in ten normal individuals), and three patients demonstrated circulating antibodies against CD42b (323±147 vs. 10±3 in normal individuals). The specificity of the assay was high, and no cross-reactivity of the sera with other platelet receptors was detected. See FIGS. 1, 2, 3, 4.

The discriminatory accuracy of the assay was assessed by means of the receiver operating characteristic (ROC) plot, that is, the graph of sensitivity vs. (1-specificity) in discriminating normal individuals from ITP patients as the threshold for the assay varies over all possible values. The area under the ROC curve (AUC) is an accuracy index ranging from 0.5 (no discrimination) to 1.0 (perfect discrimination). The results showed that at a sensitivity cut off of 85%, the specificity of diagnosis was 94%. The accuracy and sensitivity measurements represent the method and should not have to be separately determined in each laboratory.

Process 2:

A second technique was developed for the detection of platelet-antigen-specific platelet-bound auto-antibodies complex in ITP. The platelet specific antibody-antigen complex formed in vivo is isolated and immobilized on anti-platelet glycoprotein-specific monoclonal antibodies coated onto microbeads.

Further Description of the Assay Protocol

This embodiment provides an analysis of antibody-platelet antigen complexes formed in vivo.

Polystyrene beads (15 µm diameter; Polysciences, Inc. 400 Valley Road, Warrington, Pa. 18976, USA) were incubated for 2 hrs at 4° C. with monoclonal antibody against GPIIb/IIIa (20 µg/mL) final concentration; P2 clone, Immunotech, West Brook, Me., USA). The beads were then washed with PBS buffer.

Patient's platelet samples were solubilized with 0.5% Triton X-100 and centrifuged for 5 min at 1200×g. All procedures were carried out at room temperature. For the regular assay, 2500 antibody coated beads were incubated with the patient platelet lysate for 2 h, washed and then incubated for 1 h with fluorescein labeled polyclonal goat antihuman immunoglobulin antibody (20 µg/mL); Vector Laboratories, Inc., Burlingame, Calif., USA).

Then the beads were suspended with PBS and analyzed by flow cytometry. Non-specific antibody binding was measured using goat anti-rabbit antibody (Vector) with a similar fluorescein: protein ratio. The negative controls consisted of normal platelet lysate obtained from healthy individuals. The time required for the entire assay using the beads coated with monoclonal antibody is approximately 4 h. Up to 12 assays could be conveniently run at the same time.

Flow cytometric assay: Beads were initially identified and electronically gated by light scatter. One thousand events were collected for each sample. Mean fluorescence of the tested beads was determined using the standard flow cytometer software (FIGS. 5, 6, 7, 8). Statistical analysis was performed as described above. In some embodiments a method for detection of patient's circulating auto-antibodies is provided, an antigen is bound and then comes into contact with a patient's serum. In other embodiments a method comprising isolation of in vivo formed Ab-antigen complex is provided, wherein first the complex itself is isolated—patient's platelets are required—but not serum. In severe ITP it is difficult to obtain sufficient platelets for this assay, an instead the first method requiring patient's serum.

Process 3:

A third technique was developed for the determination of circulating allo-antibodies directed against platelet-specific receptors, i.e. antibodies developed against foreign platelet antigens non-existent on the patient's own platelets (similar to developing anti-Rh antibody in a Rh-negative woman exposed to Rh-positive red blood cells). The technique is based on the detection of allo-antibodies reacting with man-made microbeads coated with monoclonal antibodies directed against platelet-specific glycoproteins. The platelet glycoproteins are then immobilized on the microbead surface.

In the clinical testing, samples from patients with clinical presentation consistent with post-transfusion purpura (PTP), demonstrated antibody interaction with both CD41a complex (GPIIb/IIIa) and CD61 (GPIIIa) subunits. See FIG. 7, mean fluorescence 420±59 vs. 18±9 in normal individuals). Their allo-antibody is against an epitope on the GPIIIa subunit, these naturally form complexes with GPIIb.

Pregnant women with Neonatal-allo-immune thrombocytopenia (NAIT), a disorder which involves the development of mother allo-antibodies against her fetal platelet-glycoproteins leading to fetal thrombocytopenia and bleeding-including intra-cranial bleeds. The technique exhibits high sensitivity for diagnosis of this serious disorder, as shown in FIG. 8

The practical protocol is as described under process 1.

Process 4:

A fourth technique was developed for the detection of antigen-specific platelet-bound patient's allo-antibodies in allo-immune thrombocytopenia. The platelet specific antibody-antigen complex is isolated and immobilized on microbeads coated with glycoprotein-specific monoclonal antibody.

The antigen-specific assay for in-vivo platelet-bound antibodies was performed in adult patients with PTP and NAIT, showing a 5 to 7 fold increase of fluorescence intensity from samples of patients over samples from normal individuals, similar to the results shown in FIG. 6.

The practical protocol—is as described in process 2.

Eighteen patients with clinical diagnosis of ITP were studied. Fourteen patients demonstrated auto-antibodies against CD41a (mean fluorescence 320±137 vs. 7±2 in ten normal individuals), and three patients demonstrated circulating antibodies against CD42b (323±147 vs. 10±3 in normal individuals). The specificity of the assay was high, and no cross-reactivity of the sera with other platelet receptors was detected. See FIGS. 1, 2, 3, 4.

In conclusion, the fluorescent immunobead assay is practical, with relatively high sensitivity and specificity, and may be clinically useful for routine diagnosis and follow-up of patients with antibodies against platelet-specific glycoproteins, either auto-antibodies directed against self antigen as in TP, or allo-antobodies directed against foreign antigen as in NAIT.

The assays are applicable for various immune detection methods including fluorescence flow-cytometry and chemiluminescence microbead assay, Enzyme-linked immunosorbent assay (ELISA), also known as an enzyme immunoassay (EIA), or color microbead type of assay. It may involve single or multiple types of microbeads/microspheres varying by size (multiplex assay), internal fluorescent markers (e.g. Quantiplex™ Beads; Luminex's xMAP Technology, etc.), color markers or markers associated with magnetic material.

2. APLA/APS or Hughes Syndrome (Anti-Phospholipid-Antibody-Syndrome)

To overcome of the diagnostic limitations of currently available methods of diagnosing APS, we developed a rapid, sensitive and specific flow cytometric assay for the determination of autoantibodies directed against platelet phospholipids in antiphospholipid antibody syndrome (APS). The assay is pathophysiologically relevant since circulation platelets are a major component in the vasso-occlusive thrombotic events. The method is based on demonstrable binding of the APS patient's auto-antibodies to the platelet membrane phospholipids. This binding is detected by further incubation with the reagent fluorescence-labeled Annexin A5, which interacts with the remaining free sites on the platelet phospholipids.

We further hypothesize that since this natural reagent has anti-coagulant activity (reducing the generation of the potent coagulant thrombin on the platelet surface), occupation of its platelet binding sites by patient's antiphospholipid auto-antibodies results in an enhanced thrombin generation, thus increasing the risk for clinical thrombosis in APS.

The method is practical and rapid, uses readily available reagents, and involves standard equipment. The assay is inexpensive and cost-effective for both single and multiple samples. Results are provided within 2 hours from obtaining blood samples, thereby supporting clinical decision-making and patient management.

Overall, the assay is highly specific, allowing the reliable diagnosis of pathophyiologic ally-relevant anti-phospholipid autoantibodies.

Thus, false-positive results, obtained for example with the commonly used Anti-cardiolipin antibody tests, requiring by the international guidelines repetition after 12 weeks to rule out an incidental infectious disease, which can cause false positive results, are avoided.

The result of the present assay allows reliable diagnosis in a real-time and without a delay of this serious condition, to be followed by correct medical management.

It is important to note that this special technique has been evolutionarily developed with modifications and changes, including but not limited to 1) the preparation of a special, stable and reliable diagnostic platelet product which is suitable for routine use in regular clinical laboratories for the diagnosis of APS, and 2) special preparation of the truncated human recombinant protein annexin A5 with high fluorescein-labeling technique, for producing a sensitive reagent for the assay involving the small particles of platelets, 1-2 μm diameter.

A description of a diagnostic kit embodiment and a related method embodiment for performing the diagnostic assay are provided below.

Principles of Assay:
Preparation of Platelet Reagent:

For routine clinical laboratory use, a stable, reliable and convenient platelet reagent is prepared. The stable preparation avoids the need for fresh platelet-rich plasma-PRP for the test, and enhances its reproducibility. Platelet suspension is washed with buffer and incubated for 15 minutes with the reagent $Ca^{2+}$ ionophore A23187 (e.g. Sigma) 5 μM final concentration, for the exposure of the platelet membrane phospholipids. Then the platelet suspension is incubated with 1% paraformaldehyde for 1 hr at room temperature, and washed with buffer. The platelet preparation is finally lyophilized i.e. freeze-dried, then packed in an appropriate container for shipment and long-term storage. The paraformaldehyde followed by the lyophilization stabilize the suspension. For the assay, the platelets are resuspended in buffer to a concentration of approximately 250,000/μL, aliquots are used for the assay, and the preparation restored in a refrigerator at 4° C. for future use.

Preparation of Anti-Coagulant Low-Molecular-Weight-Heparin.

Heparin: low-molecular-weight-heparin-sodium-Enoxaparin (Sanofi—Aventis Inc, France), is prepared in concentration of—100 mg/mL. (Expiration date-very long>3 years).

Stock solution for final 10 mg/mL: 50 μL of heparin is added to 450 PBS buffer=500 μL of 10 mg/mL.

Working solution for final 2.0 mg/mL: 100 μL of heparin stock solution is added to 400 μL buffer=500 μL of 2.0 mg/mL.

To the reaction mixture of 100 μL final volume, add 5 μL of working solution heparin for a final concentration of 0.1 mg/mL.

Preparation of Labeled Recombinant Human Annexin A5 Protein.

Protein in a native form is obtained from Koa Laboratories, Tokyo, Japan. To obtain sensitive reagent suitable for testing platelets which are small particles (1-2 micron diameter), high conjugation with fluorescein-iso-thiocyanate molecules was performed. To obtain labeling with a high ratio of label to annexin, for example a protein: fluorescein ratio of about 1:6, The technology used for this procedure is as the following: All solutions and reagents are prepared in sterile water.

Materials:
0.5M Carbonate 10× Buffer as follows: Stock Solutions:
a. 5.3% Sodium carbonate. Prepare 100 ml
b. 4.2% Sodium bicarbonate, pH about 8.0. Prepare 100 ml.
Mix 58 ml of (a) with 100 ml of (b); pH will be about 9.5. Adjust pH to 9.2 with acetic acid.

Working Dialysis Buffer:
Dilute the 10× buffer 1:10 with sterile $H_2O$ and check the pH; adjust to pH 9.2 if necessary. Prepare at least 500 ml-1000 ml.

FITC Solution: (prepare fresh). Prepare 10 mg/ml in DMSO. Take from Refrigerator and bring to room temperature before weighing out.

Protein concentration should be 1-2 mg/ml to start with.
A minimum volume of 400 μl is required to obtain 0.5-1 mg from the column. To get the exact concentration of protein (if unknown) read the eluate concentration at OD 280 nm, divide by 1.4 this will give you the protein concentration of the antibody.

a column packed with cross-linked dextran gel, for example PD-10 Sephadex G-25 column, Pharmacia.
PBS w/o $Ca^{2+}$.
Sodium Azide 10% in PBS.
Method of Labeling:

Day One: the annexin antibody must be free of Na Azide (if present) and at a pH 9.2 for the fluoresceination to work. Purify the antibody, for example by dialysis: use a protein purification cassette such as Peirce's Slide-A-Lyzer for best results (follow manufacturer's directions). Place in dialysis buffer, dialyze for a minimum of 4 hrs, preferably overnight.

Day Two: Take the antibody out of the tubing very gently and measure the volume very carefully. Calculate the concentration of the antibody by taking a 50 μl aliquot and reading the absorption in a 1 cm cuvette at OD 280. The amount of antibody present is:

mg/ml antibody=(OD280/1.4)×(ml antibody)

Add 20 μg (2 μl) of the FITC Conjugate if the antibody is 2-10 mg/ml.

Add 100 μg (10 μl) of the FITC Conjugate if the antibody is <2 mg/ml.

Incubate for 60 min at 37° C. while rocking gently.

Prepare PD-10 column, place on stand, cut the tip off and place over beaker. Place a 25 cc pipette (with top cut) on top of the column; this will act as extension for the extra volume required for washing the column. Wash with 20 ml of PBS w/o Ca2+, add 500 µl of 1% BSA in PBS on top of the column and let that go through then add another 20 ml of the PBS buffer and allow that to run through. The column is now ready.

Prepare a rack with 10-15 5 ml polystyrene tubes (allowing to easily see the color of the fraction).

Run the PBS through the column until there is none remaining on top of the sintered glass. Layer the conjugated antibody to the top of the column. Allow the antibody to go into the column. Add 2 ml PBS on top of the column and let it run through. Start collecting eluent at 500 µl fractions (first fraction will be a blank). The FITC Conjugated antibody can be seen by the distinctive yellow color, once the yellow fraction starts coming through collect all at once making sure that the bulk of the fraction is collected, and that the more later diluted fractions are collected separately. This way the antibody will be concentrated in one fraction.

Protect the fractions from direct light and read the samples about 3 tubes on either side of the yellow fractions. Read the whole of the collected fraction. Use the first fraction collected as the blank read at dual wave lengths 280 nm and 495 nm. If the reading is >1.5 then dilute 50 µl with 150 µl PBS and read again.

Calculate the concentration of the conjugated antibody and the F/P ratio

Antibody Conc. mg/ml=OD280−(0.31×OD495)

1.4

F/P Ratio=(2.86×OD495)

OD280−(0.31×OD495)

Add 1% Na Azide to the collected fractions and store at 4° C.

The amount of the FITC-labeled Annexin A5 bound to the free sites on the platelets preparation is determined, and is inversely proportional to the amount of patient's autoantibody binding (FIG. 9-11) i.e. high binding is found with normal samples and low binding with APS patient samples, as shown in the figures (all the points on the scatter plots are from one sample, upper from a normal individual, lower from a patient with the condition).

Materials:
Treated platelet preparation—is prepared by the specific procedure described above.
  Annexin A5 (Koa Laboratories, Tokyo, Japan), fluorescence-labeled by the procedure for high-labeling described above.
  CD41 PE (Immunotech, Westbrook, Me., USA, or equivalent) 5
  buffer (0.02 M HEPES, 2.5 mM CaCl2, pH 7.3 in normal saline).
  Sodium citrate buffer 3.8%, or ACD-A INH formula A.
Low-molecular-weight-heparin: prepared as described in the above procedure.
Serum or plasma is prepared from patient's blood by standard centrifugation.
Protocol:
Procedure for testing patient's serum or plasma for antiplatelet phospholipid auto-antobodies.
Principles of the Assay:
APS patient's serum or plasma is incubated with the specific platelet preparation described above for the binding of the patient's antiphospholipid autoantibodies to the platelet membrane phospholipids. Similarly, normal control samples are prepared from sera or plasma obtained from healthy individuals.

Following first incubation, the platelet suspension is further incubated with the high-FITC (flurescein)-labeled Annexin A5 which occupies the remaining binding sites on the platelet membrane phospholipids.

The amount of the FITC-labeled Annexin A5 bound to the free sites on the platelets preparation is determined, and is inversely proportional to the amount of patient's autoantibody binding (FIG. 9-11) i.e. high binding of labeled-annexin is found with normal samples and low binding is found with APS patient samples, as shown in the figures.

Step 1:
5 µL of the special platelet suspension are added to 50 µL patient, negative-control (NC) and positive control (PC) serum/plasma into a tube with 45 µL HEPES buffer, containing Calcium to a final concentration 2.5 mM.

Add 5 µL of Low-molecular-weight-heparin working solution.

Incubate at room temperature for 60 minutes.
Step 2:
Add 10 µL of phycoerythrin-labeled anti-CD41 MoAb to each tube.
Add the high-FITC-labeled Annexin (final concentration 1 µg/ml) to the reaction tube.
Incubate for 15 minutes at room temperature.
Dilute with 400 µL HEPES buffer and analyze by flow cytometry.

FIGS. 9-11 illustrate exemplary results of the assays. High resolution between results from samples of APS patients and results from healthy controls is shown.

This diagnostic technology has a high potential for feasible, rapid, accurate and pathophysiologically relevant diagnosis of APS.

3. HIT (Heparin-Induced Thrombocytopenia)
To obtain reliable results, the old method [Tomer A, 1997] has been replaced by the present one, to offer a more feasible and reliable one for routine clinical use.

The method no longer comprises detecting platelet procoagulant activity associated with the exposure of anionic phospholipids on the platelet membrane. The reagents such as Annexin V which allowed detection of platelet procoagulant activity, have been replaced by new ones. The buffer used, HEPES, which required special preparation with calcium, an agent that can activate platelets by itself, was replaced by the buffer calcium-magnesium free Phosphate-buffered saline (PBS). This buffer also provides stabilization of the biochemical system. Alternatively, physiological fluid or any buffer may be used, as long as it does not contain calcium or any other agent that can activate the platelets, and allows the platelets to survive. The number of test tubes was cut by half, using only two per sample, one without and one with 0.3 U/mL heparin, instead of using four different concentrations: 0, 0.1, 0.3 and 100 U/mL heparin. The concentration of heparin may be between 0.1 and 0.5 IU/mL, and preferably about 0.3 IU/mL. Also an in vitro activation control to assure the performance of the reagents was added as TRAP (thrombin receptor agonist/activating peptide).

Whereas in the old method an immediate reading was required for reliable results, in the present one reading can be done reliably within two hours. Reproducibility is highly enhanced. The required volumes of both platelets was reduced from 70 µL to 10 µL, and patient's plasma is significantly minimized to 10 µL, allowing duplication and repetition for follow up when that is required. Thus, the present method is based on the detection of different parameters of platelet reaction to heparin, using totally different reagents, and is highly optimized, resulting in a significantly more feasible, reliable and reproducible technique, that can be performed by any regular laboratory technician, thus making it suitable and available for wide-range routine clinical diagnosis. The present method has been tested on more than 200 patients' samples and found to be in high correlation with the clinical manifestation of HIT, as it is further explained below.

In addition, this method is capable of determining any immune cross-reactivity with heparin substitute therapies, which may be administered in case of diagnosis of HIT [Alving B], [Hirsh J et al.].

Thus, the present assay is highly specific and sensitive, allowing the highly-reliable diagnosis of HIT, irrespective of the nature of the heparin complex formed in vivo. According to positive test results, the treatment with heparin needs to be discontinued immediately, and be replaced by alternative, non immune-cross-reactive anti-coagulant medication.

Method: The method is optimized for a feasible routine use in clinical laboratory, employing diagnostic kit embodiments such as described here, with simple instructions.

This optimization includes the use of inexpensive and stable reagents, determination of relative volume of each reagent in the mixture for optimal results, and minimizing the sample volumes to micro-volumes (10 μL platelet suspension & 10 μL patient's serum) to allow duplication, repetition and preservation of the patient material for future testing and monitoring.

The reaction mixture is stable allowing convenient time for reading, and the procedure is simple to carry out, with results obtainable in less than 2 hours.

The primary results were thoroughly analyzed in collaboration with a professional biostatician to determine the most feasible and reliable parameters for diagnosis.

The optimized method has been tested on a large number of patients (>200), simultaneously with other immune-detection routinely employed assays, showing both high feasibility in clinical laboratory and high reliability and reproducibly for diagnosis. Thus, the diagnostic kit materials with the practical technique described below are highly useful for the feasible, rapid and reliable diagnosis of HIT. Using ROC plot analysis for overall performance of the assay to discriminate between patients and normal individuals, a high index of accuracy was found. The area under the curve was 0.86 compared to the commercially available assay showing a parameter of 0.62. This is translated to about 30 double the sensitivity and a higher specificity of the present assay.

The method is based on the demonstration of in vitro activation of normal platelets following incubation with the patients' sera in the presence of heparin, a process imitating the in vivo pathophysiology of the disorder. The platelet response is detected by measuring the specific binding of an antibody directed against platelet CD62, an antigen that is exposed on the external platelet membrane following activation.

The technique uses standard buffers such as PBS without additions, and two-color flow cytometry, to facilitate the routine diagnosis in clinical laboratories. The procedure consists of two major steps. The first one includes incubation for 60-minutes of patient serum/plasma with normal platelets, once in the absence and once in the presence of a pharmacological concentration of heparin (0.0; 0.31 U/ml respectively (however, using a high dose of 100 U/mL as an another control remains optional for the laboratory). The second step includes the incubation for 15 minutes of an aliquot from the first step with MoAb against-CD41a for platelet identification, and with anti-platelet CD62 antibody for detection of platelet reaction.

Results are obtained from the flow cytometric analysis, and the degree of platelet activation is directly determined without further manipulation or calculations (see FIG. 12).

Following is a protocol of a proposed kit and method embodiments for the diagnostic assay of HIT.

Description of the Diagnostic Kit, Materials and Technique for Performing the Diagnostic Assay of HIT.

Materials:

a. PBS—Phosphate-buffered saline (Ca2+/Mg2+ free), (standard buffer)

b. TRAP—Thrombin-receptor activating/agonist peptide. [e.g. Calbiochem or Tocris Bioscience—MW-1739. 500 mg, dissolved into 0.5 mL Deionized/DDW=1 mg/mL. Dilute aliquots 1:1 in PBS. Add 8 μL (2 μL, final concentration), to reaction mixture of 50 μL final volume].

c. Monoclonal antibody anti-p-selectin (CD62p)—fluorescence labeled (e.g. FITC—fluorescein-iso-thiocyanate—green fluorescence, e.g. Biogen, Cambridge, Mass.; or Serotec, UK).

d. Monoclonal antibody anti-platelet CD41a (GPIIb/IIIa)—fluorescence labeled (e.g. PE—phycoerythrin—Orange fluorescence) (e.g. Immunoteck, Westbrook, Me.).

Any combination of two fluorescent probes that can be optically resolvable for analysis is applicable, (for example fluorochroms emitting at: 530/30 nm (FITC); 585/40 nm (PE, PI); 675 nm LP(PE-Cy5, PE-Cy5.5, PerCP, PerCP-Cy5.5, PE-Cy7); 675/25 nm (APC).

Blood Samples.

Five milliliter blood samples from normal individuals and from patients are collected into syringes containing 1/10 volume of 3.8% tri-sodium-citrate buffer (0.129M) (standard vacuum tubes) or ACD (acid-citrate-dextrose buffer—NIH formula A). Blood samples are gently mixed and processed without delay.

Platelet-rich plasma (PRP) is prepared by slow centrifugation (150×g for 5 min) and the platelet count is adjusted to 250,000 platelets/μL (PRP is usually between 360 and 400×109 L-1). Alternatively, PRP can be obtained from blood bank pheresis or random platelet units.

PRP-10 μL & Plasma—10 μL

Prepare the following tubes (12×75 mm BD Falcon polypropylene or equivalent).

Final reaction volume 50 μL—cap tube tightly with stopper.

Positive control/frozen sample—spin 20 min, 4° C., at high-speed to remove aggregates. Keep sample on ice.

Normal control: Platelet-poor-plasma (PPP) is prepared by higher centrifugation (2500×g for 15 min) from the PRP.

TABLE 1

I. First incubation step:
Prepare the following tubes:

| Tube # | Sample | PBS μl | Plasma μl | PRP μl | heparin 3 U/ml | Total Vol |
|---|---|---|---|---|---|---|
| 1 | Blank | 40 | 0 | 10 | 0 | 50 |
| 2 | Normal Control, NC | 30 | 10 | 10 | 0 | 50 |
| 3 | NC & heparin, NCH | 25 | 10 | 10 | 5 | 50 |
| 4 | Positive Control, PC | 30 | 10 | 10 | 0 | 50 |
| 5 | PC & heparin, PCH | 25 | 10 | 10 | 5 | 50 |
| 6 | Patient I, PI | 30 | 10 | 10 | 0 | 50 |
| 7 | PI & heparin, PIH | 25 | 10 | 10 | 5 | 50 |

More rows can be added to the table according to the number of patients.

The plasma in the NC is of a healthy individual, PC is of an individual having HIT, and Patient I has the patient's plasma without heparin, which usually provides a negative result.

Add the contents to a reaction tube in the listed order; avoid creating air bubbles.

Mix gently, place on rocker with gentle mixing at room temperature (25° C.) for 1 h.

II. Second Incubation Step:

Prepare the following tubes from each of the above tubes plus one extra for TRAP.

TABLE 2

| Tube # | Sample | PBS µl | µl PRP From first step | Anti-CD41a-PE | Anti-CD62p-FITC | TRAP µl | Total Vol |
|---|---|---|---|---|---|---|---|
| 1 | Blank | 35 | 12* | 1 | 2 | | 50 |
| 2 | NC | 35 | 12* | 1 | 2 | | 50 |
| 3 | NCH | 35 | 12* | 1 | 2 | | 50 |
| 4 | PC | 35 | 12* | 1 | 2 | | 50 |
| 5 | PCH | 35 | 12* | 1 | 2 | | 50 |
| 6 | PI | 35 | 12* | 1 | 2 | | 50 |
| 7 | PIH | 35 | 12* | 1 | 2 | | 50 |
| 8 | TRAP | 27 | 12** | 1 | 2 | 8 | 50 |
| 9 | | 27 | 12** | 1 | 2 | 8 | 50 |

*Use respective tube from Table 1.
**use PRP from Blank or NC of Table 1 without heparin..

Mix gently & incubate as above for 15 min at RT.

Stop reaction by adding 450 µl PBS.

III. Flow Cytometric Analysis—Analyze within 30 min.

Read: Flow rate—Low to Medium. Start with Blank to check reading of the cytometer, to ensure the instrument is working well.

The blank is optional; a NC sample may be used instead to check the instrument functional setting. The PC and PCH are also optional, and indeed in some laboratories and occasions may not be available. The TRAP samples assure the performance of the reagents that were added, and their contribution to the reliability of the results is a significant improvement to the test, however they too are optional. In short, the analysis samples may consist of the NC, NCH, PI and PIH, however, the blank, PC, PCH, TRAP samples, each or in combination thereof, are preferably also tested.

Analysis of the results is given below.

Obtain 5000 platelet (CD41a positive) events per tube.

Analysis. Measure two factors:

Mean total fluorescence of the total platelet population, and

% of activated particles i.e. set a marker on 2.5% (2SD of Normal distribution) of the high-CD62p-fluorescence end of the Normal control/Blank.

Calculate the difference in reading between %-activated platelets at 0.3 u/mL versus 0.0 u/mL Heparin at said high-CD62p fluorescence end.

Results: Compare said difference for patient sample to NC and PC samples. Positive results are substantially more than, for example >2.5 times, the NC difference.

4. Platelet Function Assessment

Platelet aggregometry requires large blood samples, thus it is unsuitable for diagnosis in neonates and small children. In contrast, the method described below requires sampling merely a few microliters per test, is designed to test all three important phases of platelet activation, and is highly sensitive to subtle abnormalities that might be acerbated in certain conditions such as taking aspirin or Advil, [Qureshi Z, Hobson A R.], causing bleeding. In addition, in contrast to the other methods, this method is capable of quantitatively determining the magnitude of the platelet inhibition or dysfunction.

Purpose: to assess platelet function by determination of responsiveness to stimulants, at three levels of platelet activation: A. activation of the major functional receptor GPIIb/IIIa (CD41a)—responsible for platelet aggregation via binding of fibrinogen; B. release reaction of active mediators which enhances activation and recruit ambient platelets to the site of injury, and C. expression of platelet procoagulant activity by exposure of the membrane anionic-phospholipids, which serve as binding sites for prothrombinase complex (Factor xa, Factor Va and prothrombin). This assembly highly enhances the conversion of prothrombin to thrombin—the major coagulation factor.

This stage of activation is defective for example in the serious bleeding disorder Scott Syndrome—which gives normal results in the clinical platelet aggregation assay [Reference 1,2].

For detection of either subtle abnormalities or inhibition of platelet function by anti platelet drug, full quantitative assessment by a simple and feasible dose-response assay may be performed.

The diagnosis of platelet dysfunction by this sensitive and informative technique mandate the discontinuation by the physician of medications affecting platelet function, such as very commonly used non-steroidal anti-inflammatory drugs (NSAID), Ibuprofen-Advil$^R$ and Aspirin, and providing appropriate treatment to enhance hemostasis (e.g. tranexamic acid, etc.).

Diagnostic kit materials and related techniques for performing the diagnostic assay for platelet function.

Stages A and B-Detection of Activation of the Major Functional Receptor CD41a and of Active Mediators—Kit and Method Materials.

Buffers:

PBS—Ca2+ and Mg2+ free (e.g. 0.5 L, Cellgro).

3.8% citrate buffer or ACD (acid-citrate-dextrose buffer—NIH formula

Stimulants: ADP, TRAP.

Monoclonal antibodies (MoAb)

anti-glycoprotein (GP) IIb/IIIa (CD41a), (Immunotech, Westbrook, Me., or another vendor).

anti-P-selectin (CD62p) (Biogen, Cambridge, Mass., or another vendor)

PAC-1, against the activated conformation of glycoprotein IIb/IIIa (Becton Dickinson Biosciences, CA), Alternatively, LIBS (ligand-induced binding site), and RIBS (receptor-induced binding site on the platelet-bound fibrinogen molecule), or fibrinogen.

Stimulating agents/Platelet agonists:

TRAP—Thrombin-receptor activating/agonist peptide. [e.g. Calbiochem or Tocris Bioscience—MW:1739. 500 mg, dissolved into 0.5 mL Deionized/DDW=1 mg/mL. Dilute aliquots 1:1 in PBS. Add 8 µL to reaction mixture of 50 µL final volume].

ADP, Sigma, dissolved in PBS or normal saline to a concentration of 1 mM. Stock solution is 10×, to be added as ⅒ of the volume).

Tubes—Polypropylene tubes (12×75 Becton Dickinson, San Jose, Calif., or similar product).

Platelet-rich plasma (PRP) preparation:

For PRP-2 to 4 mL blood samples are collected into syringes containing ⅒ volume of 3.8% citrate buffer or ACD or into tubes containing citrate—a standard tube for coagulation assays. (for small children whole blood-50 µL, neonates-20 µL)

To minimize sample manipulation, the blood sample is gently mixed, transferred into a tube and processed without delay.

PRP is prepared by standard slow centrifugation (150×g for 5 min); the platelet count is adjusted to 250,00 platelets/µL with Ca2+, Mg2+ free PBS, and the PRP is kept in a polypropylene tube.

Assessment of Platelet Responsiveness—Platelet Stimulation and Labeling.

General: Platelets are stimulated with ADP or TRAP and labeled with specific monoclonal antibodies for the detection of activation markers.

Five µL aliquots of PRP are diluted with 45 µL PBS in polypropylene tubes and simultaneously incubated with:
 a. 2 µL of phycoerythrin-labeled MoAb against the glycoprotein (GP) IIb/IIIa (CD41a) for immune detection, and
 b. 2 µL fluorescein-labeled MoAb against P-selectin (CD62p), an α-granule membrane glycoprotein expressed on platelet surface following secretion; or
 c. 5 µL fluorescein-labeled MoAb PAC-1 (use b. or c.).

Platelets are stimulated with:
 a. ADP, 5 µM final concentration; or
 b. TRAP, 4 µM final concentration;

For dose-response studies platelet samples are incubated with either ADP 0, 2.5, 5.0 and 10 µM ADP final concentrations; or TRAP 0, 1.0, 2.0, and 4.0 µM.

Labeled samples are incubated for 30 min at room temperature.

Following incubation, 450 µL of PBS buffer are added and samples are analyzed by flow cytometry.

Flow Cytometric Analysis of Platelets.
 a. Platelets are initially detected by light-scatter.
 b. To fully resolve the small platelet particles from electronic noise and cell debris, platelets are distinguished by the specific immunofluorescence (FL2, yellow fluorescence bandpass) of the anti-GPIIb/IIIa antibody.

The platelet population is then electronically selected/gated and analyzed for activation as determined by the specific fluorescence (FL1, green fluorescence bandpass) of platelet PAC-1 bound with anti-p-selectin monoclonal antibody.
 c. Single-fluorescent color preparations are used to correct for emission spectra overlap (compensation).

Acquisition rate is limited to 1000 platelets/sec to prevent coincidental detection of more than one particle.

Five to ten thousand platelets (FL2-gated events) are collected for each sample and analyzed using the flow cytometry.

Platelet activation is determined by: a) Mean total fluorescence of the total platelet population, and b) % of highly-activated platelets by setting a marker on 2.5% (2SD of Normal distribution) of the high end of the CD62p-fluorescence distribution curve of the normal control or patient non-stimulated sample.

Optional: three-color analysis involving all three antibody probes, wherein the third one is labeled with a fluorochrome compatible with FITC & PE, such as, but not limited to, PerCP of Becton Dickinson, tandem PE-Cy5 or other PE-Cy emitting beyond the range of PE (see details in Section: Flow Cytometer below).

Stage C—Detection of Platelet Procoagulant Expression—Materials and Methods.

Stimulants: $Ca^{2+}$ ionophore A23187

Detection probes: Annexin A5.

Materials:
 Annexin A5—fluorescein-labeled; avidly binds to anionic-phospholipids expressed on platelet surface following full activation.
 $Ca^{2+}$-Ionophore A23187 (e.g. Sigma), 5 µL/50 µL platelet suspension (50 µM final concentration) for platelet stimulation.
 anti-glycoprotein (GP) IIb/IIIa (CD41a) MoAb, (Immunotech, Westbrook, Me., or another vendor) for immune detection of platelets.
 HEPES buffer containing calcium: (0.02 M HEPES, 2.5 mM CaCl2, pH 7.3 in normal saline).
 3.8% citrate buffer or ACD (acid-citrate-dextrose buffer—NIH formula A)
 Polypropylene tubes (12×75 Becton Dickinson, San Jose, Calif.)

Note that the fluorescence labeling can vary between different vendors—any combination suitable for the detection can be used.

Platelet-rich plasma (PRP) preparation:
A 5 mL blood sample from each patient is collected into a syringe containing 1/10 volume of 3.8% citrate buffer or ACD, or into tube containing citrate—a standard tube for coagulation assays. Normal control PRP can be obtained from blood bank pheresis or random platelet units.

To minimize sample manipulation, blood sample is gently mixed, transferred into a tube and processed without delay.

PRP is prepared by standard slow centrifugation (150×g for 5 min); the platelet count is adjusted to 250,000 platelets/µL with Ca2+, Mg2+ free PBS and the PRP is kept in polypropylene tubes.

Platelet Stimulation and Labeling.

General: Platelets are stimulated with Ca2+-Ionophore and incubated with fluorescein-labeled Annexin A5, which avidly binds to anionic-phospholipids expressed on platelet surface following full activation. Platelet particles are identified by the fluorescence of anti-GPIIb/IIIa MoAb (CD41a), then electronically selected (gated).

5 µL aliquots of PRP are diluted with 45 µL HEPES buffer in polypropylene tubes and simultaneously incubated with:
 2 µL phycoerythrin-labeled MoAb against platelet GPIIb/IIIa (FL2).
 2 µL fluorescein-labeled Annexin A5 (FL1).

Platelets are stimulated with Ca2+-Ionophore, 5 µL per 50 µL platelet suspension (50 µM final concentration).

Following incubation for 15 min at room temperature, 450 µL of HEPES-Ca2+ buffer are added and samples are analyzed by flow cytometry.

Flow Cytometric Analysis of Platelets.

Platelets are initially detected by light-scatter.

To fully resolve the small platelet particles from electronic noise and cell debris, Platelets are distinguished by the specific immunofluorescence of anti-GPIIb/IIIa MoAb (FL2). The platelet population is then electronically selected/gated and analyzed for activation as determined by the binding of fluorescein-labeled Annexin A5 (FL1).

Single-fluorescent color preparations are used to correct for emission spectra overlap (compensation)

Acquisition rate is limited to 1000 plts/sec to prevent coincidental detection of more than one particle.

Five to ten thousand platelets (CD41a-FL2-gated events) are collected for each sample and analyzed using the flow cytometric software.

The fraction of activated events is determined by setting a marker at 2.5% (2SD of Normal distribution) of the right-end of the Annexin V-FL1 histogram/dot-plot presentation of the non-stimulated sample, and measurement of the number of events (% of total) beyond that point on the fluorescence scale in the stimulated patient sample.

This feasible and rapid assay may provide highly useful information to the physician regarding the nature of and the magnitude of the platelet functional abnormality, thus assisting in both diagnosis and design of appropriate medical intervention appropriate for the patient.

5. Platelet Receptor Deficiencies/Abnormalities—Glanzmann Thrombasthenia and Bernard-Soulier Syndromes.

The purpose of the following technique is the accurate and feasible clinical diagnosis of these disorders, thereby eliminating unnecessary treatment, and dictating the appropriate medical management for these life-long bleeding disorders.

The description of the diagnostic kit and related technique to be used in routine clinical laboratories are given below.

Materials:
Samples: 50 μL whole-blood or Platelet-rich plasma (PRP) in duplicates.
Monoclonal Antibodies—MoAb:
anti-Glycoprotein (GP) IIb/IIIa (e.g. P2, AP2 clone)
anti-GP IX (e.g. SZ1/GPIb-IX-V complex(CD42b))
anti-GP IIb (e.g. M148)
anti-GP IIIa (e.g. AP3)
anti-p-selectin (CD62-p) (e.g. AK)
anti-Fibrinogen (e.g. E7)
anti-human IgG (to rule out presence of an autoantibody such as ITP which may interfere with testing of MoAbs), and
labeled fibrinogen.
These reagents are selected according to the clinical question being asked for evaluation—as also specified below.
Saponin—for red-blood cell lysis (0.5% w/v saponin—e.g., Sigma cat No S-7900)
Fixative: Formaldehyde (e.g. Fischer Scientific) 1% in PBS+3 mM EDTA 5% W/Volume.
Method:
Fix (fresh sample or stored sample—storing good for 3-days at 4° C.) sample: to 50 μL whole-blood, add 450 μL of PBS+PGE1 (prostaglandin E1) to 20 μM final concentration. Add 1.5 mL of standard fixation buffer, mix and incubate 15 min at RT. Centrifuge 250 g for 5 min, decant supernatant and wash twice with PBS. Resuspend in PBS and store at 4° C.

Lysis—to 40 μL of cell suspension add 60 μL of saponin solution, wait 10 min at RT then centrifuge 250 g for 5 min and resuspend in 50 μL PBS.

Flow Cytometric Assay

To 2 μL cell suspension add 45 μL PBS and 1-2 μL of fluorescence-labeled MoAb;

Incubate for 30 min at RT; dilute with 450 μL PBS and analyze by flow cytometry; use "live-gate" to eliminate red-cell debris; collect 5,000-10,000 platelet events, and compare results between the various antibodies, and with a normal control. The results are compared and analyzed using standard flow cytometric software—see for example FIG. 13.

FIG. 13 shows the results of analysis of blood platelets for the expression of membrane glycoproteins by Flow Cytometry. The Patient shows normal expression of GPIIb/IIIa but deficient expression of GPIb, a characteristic of Bernard—Soulier Disease. A child of the patient shows intermediate expression of GPIb, indicating a carrier state, as is shown by the degree of the measured immunofluorescence, of the anti-PGIb specific antibody.

FIG. 14 demonstrates the accuracy of this flow cytometric technique determination, with high correlation between the binding of FITC-labeled and $^{125}$I-labeled anti-GPIb antibodies to platelets. Three groups are identified, Patient with severe deficiency (lower-left corner), three relatives with intermediate expression (middle of the graph) representing a carrier state, and normal controls (upper-right). Thus, this technique is highly reliable and sensitive not only for diagnosis of severe deficiency in patients with Bernard-Soulier disease, but also for detection of partial expression by carrier individuals, which is important for genetic counseling, before marriage for example.

6. Platelet Function Inhibition by Anti-Platelet Drugs (e.g. Aspirin and Thienopyridine Agents Such as Clopidogrel-Plavix$^R$)

To identify a condition of platelet function inhibition by anti-platelet drugs following treatment and to make dose adjustments or change the agent, testing the inhibitory effect of the anti-platelet drugs on platelet function is required. This can be achieved by the determination of patient's platelet responsiveness to agonists (platelet stimulators) relevant to the drug inhibitory pathway. Testing the stimulatory effect of the anti-platelet drugs on platelet function can preferably be performed prior to starting treatment to provide baseline measurement for therapy testing.

Based on the results of the test, the dose of the anti-platelet drug being used may be modified, discontinued and substituted by a different anti-platelet drug, or combined with another anti-platelet drug (dual anti-platelet therapy), as might be decided by the clinician.

Currently available methods for determination of platelet function inhibition by anti-platelet drugs have a very limited value primarily due to methodological and practical limitations, especially lack of quantitative assessment, and none are recommended by national or international professional societies.

The technique described below is feasible, sensitive, quantitative and highly informative, allowing the reliable assessment of the inhibitory effect, and permitting therefore a rationally-based and appropriate medical management. Its effectiveness can be further tested and adjusted according to the patient's needs.

A Description of Diagnostic Kit Materials and a Related Technique for Performing the Diagnostic Assay of Drug Inhibitory Effect.

Technique:
Two strategies are employed: a) assessment of platelet responsiveness at the specific three stages of physiological activation process by using the specific probes mentioned; and b) performing quantitative determination for the degree of inhibition, by short dose-response assay of the stimulants (3-4 points). The assessments are compared to results from normal control platelets, and the ED50 (the concentration of platelet agonist causing 50% response) is quantitatively determined. Patients may also be tested prior to initiating therapy, thus, their individual own platelets could serve as a reference for comparison. This fully informative approach has never been applied by other methods. The description of the diagnostic kit and related technique is given below.

Laboratory Technique for Quantitatively Assessing the Inhibitory Effect of the Anti-Platelet Drugs on Platelet Function.

Materials:
Stimulators:
a) Arachidonic acid—for the inhibitory effect of Aspirin;
b) ADP—for the inhibitory effect of thienopyridine agents such as Clopidogrel-Plavix$^R$, Prasugrel$^R$ and Ticagrelor$^R$.
c) TRAP—for both.

d) Ca$^{2+}$ ionophore A23187—for the expression of procoagulant activity.

Detection Probes:
a) MoAb PAC-1 for activated of GPIIb/IIIa receptors;
b) MoAb anti-P-selectin which labels a selectin receptor exposed on the platelet surface upon its activation, and
c) Annexin A5 for detection of platelet procoagulant activity.

For dose-response studies, platelet samples are incubated with final concentrations of:
1. ADP 0, 2.5, 5.0 and 100 μM ADP final concentrations;
2. Arachidonic acid, 0, 0.25, 0.50, and 0.75 mM, final concentration.
3. TRAP 0, 1.0, 2.0, and 4.0 μM, final concentration.
4. Ca$^{2+}$ ionophore A23187, 0.5, 1.0, 2.0, and 30 μM final concentration Platelet Activation and Labeling.

General: Platelets that are stimulated with ADP, Arachidonic acid or TRAP, are labeled with specific monoclonal antibodies for the detection of activation markers, activated glycoprotein (GP) IIb/IIIa (CD41a), and expression of p-selectin (CD62p)-which is an α-granule membrane glycoprotein expressed on platelet surface following secretion.

Five μL aliquots of PRP are diluted with 45 μL PBS in polypropylene tubes and simultaneously incubated with:
a. 2 μL of phycoerythrin-labeled MoAb against the glycoprotein (GP) IIb/IIIa (CD41a) for immune detection, and
b. 2 μL fluorescein-labeled MoAb against P-selectin (CD62p), an α-granule membrane glycoprotein expressed on platelet surface following secretion; or
c. 5 μL fluorescein-labeled MoAb PAC-1—for activated GPIIb/IIIa (CD41a).

For dose-response studies platelet samples are incubated with 3 different stimulators: ADP: 0, 2.5, 5.0 and 100 μM ADP final concentrations, b) Arachidonic acid: 0, 0.25, 0.50, and 0.75 mM, final concentration, or c) TRAP: 0, 1.0, 2.0, and 4.0 μM, final concentration.

Labeled samples are incubated for 30 min at room temperature.

Following incubation, 450 μL of PBS buffer are added and samples are analyzed by flow cytometry.

Flow Cytometric Analysis of Platelets.
a. Platelets are initially detected by light-scatter.
b. To fully resolve the small platelet particles from electronic noise and cell debris, Platelets are distinguished by the specific immunofluorescence (FL2) of the anti-GPIIb/IIIa binding of phycoethrin-labeled MoAb.

The platelet population is then electronically selected/gated and analyzed for activation as determined by the binding of anti-p-selectin, or PAC-1 monoclonal antibody (FL1).

c. Single-color preparations are used to correct for emission spectra overlap (compensation).

Acquisition rate is limited to 1000 platelets/sec to prevent coincidental detection of more than one particle.

Five to ten thousand platelets (FL2-gated events) are collected for each sample and analyzed using flow cytometry.

Platelet activation is determined by: a) Mean total fluorescence of the total platelet population, and b) % of highly-activated platelets by setting a marker on 2.5% (2SD of Normal distribution) of the high end of the CD62p-fluorescence distribution curve of the Normal control or patient non-stimulated sample.

Quantitative determination of inhibitory effect: For each platelet stimulant, the degree of response at each concentration, defined as the degree of the patient's platelet response to stimulant (e.g. fluorescence level of the specific probe), is plotted against the concentration of the specific stimulant, and the ED is calculated, as the dose of the platelet agonist induced half-maximal—50%—activation. The patient's ED50 is then compared to normal control and the degree of platelet inhibition is quantitatively determined. This determination may be repeated in future following modification of therapy to assess treatment efficacy.

Responsiveness of platelet procoagulant activity. (assessment of the inhibitory degree of the anti-platelet medication on the expression of platelet procoagulant activity which normally augments thrombin generation, leading to clinical theombosis)

Stimulators: Ca$^{2+}$ ionophore A23187.

Detection probes: Annexin A5.

Materials:
Annexin A5—fluorescein-labeled; avidly binds to anionic-phospholipids expressed on platelet surface following full activation.
Ca$^{2+}$-Ionophore A23187 (e.g. Sigma), added 5 μL per 50 μL platelet suspension.
anti-glycoprotein (GP) IIb/IIIa (CD41a) MoAb, (Immunotech, Westbrook, Me., or other vendor).
HEPES buffer containing calcium: (0.02 M HEPES, 2.5 mM CaCl$_2$, pH 7.3 in normal saline).
3.8% citrate buffer or ACD (acid-citrate-dextrose buffer—NIH formula A)
Polypropylene tubes (12×75 Becton Dickinson, San Jose, Calif.)
(the fluorescence labeling can vary by different vendors—any combination suitable for the detection can be used)

Platelet-rich plasma (PRP) preparation:
5 mL blood samples are collected into syringes containing ⅒ volume of 3.8% citrate buffer or ACD, or into tube containing citrate—standard tube for coagulation assays. Alternatively, PRP can be obtained from blood bank pheresis or random platelet units.

To minimize sample manipulation, blood samples are gently mixed, transferred into a tube and processed without delay.

PRP is prepared by standard slow centrifugation (150×g for 5 min); the platelet count is adjusted to 250,000 platelets/μL with Ca$^{2+}$, Mg$^{2+}$ free PBS and the PRP is kept in the polypropylene tube.

Platelet Stimulation and Labeling for Procoagulant Activity.

General: Platelets are stimulated with Ca$^{2+}$-Ionophore and incubated with fluorescein-labeled Annexin A5, which avidly binds to anionic-phospholipids expressed on platelet surface following full activation. Platelet particles are identified by the fluorescence of anti-GPIIb/IIIa MoAb, then electronically selected (gated).

5 μL aliquots of PRP are diluted with 45 μL HEPES buffer (pH=about 7.4 in polypropylene tubes and simultaneously incubated with:
2 μL phycoerythrin-labeled MoAb against platelet GPIIb/IIIa (FL2).
2 μL fluorescein-labeled Annexin A5 (FL1).
Platelets are stimulated with Ca$^{2+}$-Ionophore, 0.5, 1.0, 2.0, and 30 μM final concentration, added in 50 μL per 50 μL platelet suspension.

Following incubation for 15 min at room temperature, 450 μL of HEPES-Ca$^{2+}$ buffer are added and samples are analyzed by flow cytometry.

Flow Cytometric Analysis of Platelets for Procoagulant Activity

Platelets are initially detected by light-scatter.

To fully resolve the small platelet particles from electronic noise and cell debris, Platelets are distinguished by the specific immunofluorescence of anti-GPIIb/IIIa MoAb (FL2). The platelet population is then electronically selected/gated and analyzed for activation as determined by the binding of fluorescein-labeled Annexin A5 (FL1).

Single-fluorescence color preparations are used to correct for emission spectra overlap (compensation).

Acquisition rate is limited to 1000 platelets/sec to prevent coincidental detection of more than one particle.

Five to ten thousand platelets (CD41a-FL2-gated events) are collected for each sample and analyzed using the flow cytometric software.

The fraction of activated events is determined by setting a marker at 2.5% (2SD of Normal distribution) of the right-end of the Annexin V-FL1 histogram/dot-plot presentation of the non-stimulated platelet sample, and measurement of the number of events (% of total) beyond that point on the fluorescence scale.

Quantitative determination: For each platelet stimulant, the degree of response at each concentration, defined as the % of the patient's platelet response (as indicated by the binding of the specific probe), is plotted against the concentration of the specific stimulant, and the ED50 is calculated, as the dose of the platelet agonist inducing half-maximal—50%—activation. The patient's ED50 is then compared to normal control and the degree of platelet inhibition is quantitative determined. This determination may be repeated in future following modification of therapy to assess treatment efficacy.

Based on the results obtained by the assay, the dose of the anti-platelet drug being used may be modified, discontinued and/or substituted by a different anti-platelet drug, or combined with another anti-platelet drug (dual anti-platelet therapy), as decided by the clinician.

7. Platelet Activation Markers as an Indicator of Ongoing Real-Time In Vivo Prothrombotic Activity.

The goal of this technique is the determination of circulating platelet activation markers as indicators of ongoing, real-time in vivo, prothrombotic activity, to be used in routine clinical laboratories, and at point-of-care e.g. in ICCU—intensive cardiac care units or ER-emergency department. The clinical goal of the assay is the measurement of prothrombotic activity in patient's blood to permit rationally-based medical preventive intervention with anticoagulant therapy, with/or without anti-platelet drugs.

The assay is applicable for detection of ongoing hypercoagulable state in patients at risk for developing thrombosis including—but not limited to:

a. Patients with coronary artery disease (CAD). Patient with angina pectoris—stable or unstable—acute coronary syndrome (ACS), or post myocardial infarction (MI);

b. Patients with peripheral vascular disease (PVD), including cerebrovascular disease (brain circulation disorder), patient with transient-ischemic-attack (TIA), or stroke;

c. Diabetes—highly associated with vascular disorders;

d. Hypertensive disorder of pregnancy including thrombosis, pre-eclampsia, fetal growth restriction, and fetal death;

e. Patients with thrombophilic risk factors, including: antiphospholipid syndrome (APS/APLA), FV-Leiden, FIT mutation, anticoagulant protein deficiency: Protein C, protein S, and ATIII—especially if associated with additional hypercoagulable risk factor such as pregnancy, delivery, surgery, trauma and reduced mobility;

f. Patients having ongoing prothrombotic activity prior to and after cessation of anticoagulant therapy such as warfarin therapy, and g. Cancer patients, as cancer is a clinical state known to be associated with significantly increased risk for thrombosis (second cause of death after the malignancy itself).

A description of diagnostic kit materials and a related technique for performing the diagnostic assay of circulating activation markers are given below.

Materials and Method for Detection of Platelet Activation Markers

The technique has been refined for practical routine use, with reliable results. No preparation of special buffers such as Tyrod's or HEPES/Tyrod's modified buffer is required, only standard, stable, and commercially available buffers and reagents are used. Also all aspects of testing have been refined with minimal manipulation or no manipulation of specimen, minimal incubation time, minimal reagent use for lowering its cost for the public, minimal step-usually only one, and very quick reading—in few minutes. All that to make the assay suitable for wide routine clinical use, allowing testing of all necessary conditions without significant limitations for the laboratory or the patient.

Antibodies/Protein Probes:

All antibodies mentioned below include: unlabeled, fluorescence labeled, magnetic, or enzyme-labeled antibodies or protein probes (when the antibodies are unlabeled, a secondary labeled antibody may be added in an additional step).

a) Anti-CD41a (GPIIb/IIIa)—for immune-detection of platelets and platelet-related particles.

b) Anti-CD62p (p-selectin)—an α-granule glycoprotein expressed on platelets following activation and release reaction, i.e. following stimulation, release from the platelet granules of active mediators (ADP, ThromboxanA2, Serotonin, stored coagulation factors) to enhance activation and to recruit ambient platelet to the site of vessel/endothelial injury (see FIGS. 15, 16).

c) Anti-CD63/LAMP-1/LAMP-2—lysosome-associated membrane protein expressed upon release reaction.

d) Annexin A5—for detection of platelet procoagulant activity.

Annexin A5 avidly binds to the platelet anionic-phospholipids exposed on the external platelet membrane following high activation. The platelet anionic-phospholipids serve as binding site for the Prothrombinase complex (Factor Xa, Factor Va and Prothrombin), which enhances the conversion of prothrombin to thrombin—the major coagulation factor involved in thrombus formation. Annexin A5—is either in native form or is a recombinant protein.

The assay permits the detection of both activated platelets and platelet-related particles in the patient circulation. See FIGS. 15 and 16: The scatter graphs plot side scattered light (SSC light) intensity against fluorescence intensity—FL1, for normal control and for patients. SSC −90° is influenced by cell inner structure such as granules.

The patient plots indicate ongoing, real-time procoagulant/prothrombotic activity in the blood, calling for therapeutic intervention.

e) PAC1/or LIBS (ligand-induced binding site) family antibodies—for detection of GPIIb/IIIa receptor activation on platelet surface.

f) RIBS—interacts with receptor-induced binding site on the fibrinogen molecules which bind to activated GPIIb/IIIa receptor.

g) Fibrinogen—binds to activated GPIIb/IIIa receptor.

h) The activation markers may also include i) Platelet-monocyte conjugates, and platelet-granulocyte complexes formed following activation, using specific monoclonal antibodies, and ii) proteins in circulation as surrogate markers for patient's evaluation: platelet-factor 4 (PF4) & beta-thromboglobulin (β-TG), C-reactive protein (CRP), and D-dimers of fibrin degradation products.

Detection Techniques:

Platelet activation membrane markers are suitable for detection by flow-cytometry (FCM) or chemiluminescence measurement methods, but may also be detected by immobilization of the platelets on a surface followed by detection using the appropriate antibody and protein probes. Markers indicated in section h), ii) above may be detected by any immunological or biochemical method.

Platelet Stimulants for Control:

Adenosine-di-phosphate (ADP).

TRAP (Thrombin-receptor Activating/Agonist Peptide).

$Ca^{2+}$ Ionophore—A23187.

Buffers:

PBS—$Ca^{2+}/Mg^{2+}$ free. 0.5 L (e.g. Cellgro).

HEPES buffer—e.g. in an apoptosis kit (0.02 M HEPES, 2.5 mM $CaCl_2$, pH 7.3 in normal saline).

ACD—acid-citrate-dextrose buffer—NIH formula A.

Method:

Blood Samples.

5 milliliter blood samples are collected from each patient into a syringe containing 1/10 volume of 3.8% tri-sodium-citrate buffer (0.129M) or ACD. Platelet-rich plasma (PRP) is prepared by slow centrifugation (150×g for 5 min) and the platelet count is adjusted to 250,000 platelets/μL.

Platelet Labeling

For detection of membrane activation markers.

Briefly, 5 μL aliquots of PRP or whole blood are incubated with monoclonal antibody (MoAb) against GPIIb/IIIa (CD41a) complex for immune detection of platelets. For the detection of activation markers, the PRP is simultaneously incubated with MoAb:

a) PAC1/LIBS for activated GPIIb/IIIa, or RIBS for fibrinogen;

b) anti-P-selectin (CD62p) or anti-CD63 MoAb, and c) Annexin A5 protein.

Each of these probes detects a different physiological phase of a platelet activation process.

Isotype-matched MoAbs (MoAbs with genetic variations in the constant regions of the heavy/light chains) are used for negative control of nonspecific binding, and in-vitro platelets stimulated with ADP, TRAP and $Ca^{++}$-ionophore A23817 are used as positive control. Incubation is carried out in polypropylene tubes (12×75 Becton Dickinson, San Jose, Calif. or equivalent), at room temperature for 30 minutes. Following incubation, 450 μL of buffer are added and samples are analyzed by flow-cytometry or chemiluminescence or any method for the detection of antibody reacting with antigen.

Flow Cytometric Analysis of Platelet Activation Markers:

Platelets are analyzed for membrane activation markers using commonly available flow cytometry analyzers (e.g. of Coulter-Beckman; Becton Dickinson; Accuri Cytometers, Partec or other companies). Acquisition rate is limited to 1000 platelets/sec to prevent coincidental detection of more than one particle. Data on 5,000 to 10,000 platelets per sample are collected and analyzed. Initially, platelets are detected by light-scatter, and then fully resolved from electronic noise and cell debris by the specific immunofluorescence. The platelet population or related particles is electronically selected (gated) and analyzed for activation as detected by the binding of the specific probes. The average immunofluorescence of the total population or the fraction of activated events (as with Annexin A5) is determined and compared to control samples.

Example of this analysis is shown in FIG. 15 (in vivo expression of CD62p following platelet release reaction) and FIG. 16 (in vivo expression of platelet procoagulant activity).

Chemiluminescence—Measurement and Analysis of Platelet Activation Markers:

The measurements are performed as described above, using MoAb's and activation probes (e.g. Annexin A5) labeled appropriately for chemiluminescence (light detection). Instrumentation may be for example a PATHFAST Compact Chemiluminescent Immunoassay System with a MAGTRATIONR magnetic separation technology, or the LPIA-NV7, a bench-top automated immunoassay system, both made by Mitsubishi (e.g. Mitsubishi Kagaku Medical, Mitsubishi Chemical Europe GmbH).

Overall Summary of the System

The purpose of the above described Platelet Analysis System is to provide a feasible means for comprehensive assessment of common platelet—associated clinical disorders, using preferably a single dedicated instrument with effective reagent kits and feasible and practical method of analysis.

The platelet analysis system for the diagnosis of platelet-related disorders may consist of specific diagnostic kits as embodiments to be used according to the tests and diagnoses that the clinical laboratory is required to perform.

Small laboratories aimed for particular diagnoses, Cardiology or Emergency departments, for example, may select particular kit or kits for their diagnostic needs. However, some embodiments are fully applicable for central hematology or coagulation laboratories dealing with the entire range of blood clotting problems, including tendency to bleeding on one hand and thrombosis on the other hand.

The optimized techniques and kits for diagnosis of platelet—related disorders described above can be performed fairly easily at regular clinical laboratories of any scale, in contrast to formerly used tests, that required special skills and equipment typically available only at central hematological or research laboratories.

Evaluation of platelet-related conditions such as thrombocytopenia may require three tests or more, e.g. for ITP, APS (may be associated with thrombocytopenia), HIT-heparin induced thrombocytopenia, and Bernard-Soulier syndrome. For example, a patient was referred for removal of spleen for ITP—and was found by the method described above as not suffering from ITP, and was saved from unnecessary surgery. Therefore, the system as one unit for appropriate evaluation of platelet disorder comprises kits, such that the system is suitable for performing more than one assay, to achieve correct diagnosis, and prevent misdiagnosis with unnecessary or wrong therapy, as said patient had also received for many years.

Using micro volumes of blood, the assays are fully applicable for newborn and small children, which so far could not be tested for platelet functional abnormality. In particular, special attention was paid to adjust, refine and simplify the assays and their related kits providing the reagents at optimal concentrations and economical volumes, thereby requiring minimal steps and skill in performing the analyses efficiently and accurately. Providing rapid and reliable results should effectively assist the clinician with diagnosis and decision making for appropriated medical intervention.

Instruments such as flow cytometers for performing the tests may be pre-adjusted, thus made dedicated for platelet analysis. Furthermore, instruments can be customized for performing one or more of the tests to be carried out, even for Point-of-care testing, thus simplifying both their structure and their operation to provide quick results.

Flow Cytometer for the Platelet Analysis System.

The cytometers are simply designed, yet powerful, dedicated flow cytometers (FCM), adjusted specially adjusted by both hardware and software for analysis of blood platelets which are the smallest particles in blood, 1-2 µm diameter, for optimal separation from electronic noise and cell debris. The dedicated FCM is inexpensive, easy to use, require minimal maintenance and be compact, aimed for routine use in small as well as large clinical laboratories, and without the need of special skills. This dedicated FCM should allow the performance of platelet testing in a wide range of laboratories—making the necessary assays available for the common patients' population.

Basic Features Include:

High quality data;

Ability to detect forward and side light-scatter and up to 4 fluorescent colors;

Both blue and red lasers for excitation—however, a single Argon-ion laser with emission at 488 nm might be sufficient for most applications;

Easy-to-use software;

Low-maintenance and quick to install and taking up little space in the labs;

Simply operated, user friendly, equally accessible to experts and new users.

Sized to fit on any bench top in a lab.

The Fluidic System:

Is reliable, with a high performance fluidics system;

Meters sample fluid uptake and automatically calculates the events per microliter—especially important in counting low platelet number as in Immune thrombocytopenia;

Allows the user to independently adjust speed of the sample uptake;

The Optical System:

Arrangement designed for any of 4 fluorescent detectors to read from either red or blue lasers;

Allows the user to easily swap out interference filters,

Simple—capable of detecting particles with size>0.5 µm;

Electronics:

Four decades range for the fluorescence signal;

Linear dynamic response for the fluorescence signal over a 4-decade logarithmic range;

Has voltage and amplifier gain controls on the photomultiplier tube (PMT) detectors;

Allows observing a wide range of signals, to include both faint signals and bright signals;

Displays 4 full logarithmic decades, of digital data, with high resolution of signals;

Dynamic adjustment obviating the need for routinely adjusting voltage and gain settings, Preferably, capable of interfacing with a USB plug on a standard PC or laptop, computer and Simple—uses fewer components.

FCM Software:

Electronically adjusted for analysis of platelets and platelet signals;

Usable on any standard PC or laptop with >2 GB of RAM;

Is intuitive and does not require training classes;

Meets the needs of both novice and proficient users;

Eliminates layers of complexity, decreasing the learning curve;

Uses the FCS 3.0 file format, making it compatible with other software,

Allows drag and drop of plot images to MS Office and copy and paste statistics to spreadsheet programs.

Technical Features of Exemplary Instrument:

Laser Excitation:

488 nm; 50 mW diode 640 nm; 30 mW diode;

Laser profile: 15×50 microns;

Light Scatter detection: Forward (0 degrees) & Side (90 degrees);

Fluorescence Emission detection: 4 colors: 530/30 nm (FITC); 585/40 nm (PE, PI); 675 nm LP(PE-Cy5, PE-Cy5.5, PerCP, PerCP-Cy5.5, PE-Cy7); 675/25 nm (APC);

Optical alignment: Fixed alignment, no maintenance required;

Fluorescence sensitivity: <750 MESF FITC

Fluorescence precision: <3% CV for chick embryonic nuclei (CEN);

Light Scatter resolution: capable of highly resolving platelets from peripheral blood cells;

Cell counting Speed: up to 5,000 events/second;

Power: 70 Watts maximum, 100-240 VAC, 50/60 Hz;

Instrument size: Approximately-11.5"H×14.6"W×16.6"D (30.2×37.0×42.0 cm), and

Instrument Weight: Approximately 29 lb (13.2 kg)

BIBLIOGRAPHY

Tomer A, Human marrow megakaryocyte differentiation: multiparameter correlative analysis identifies von Willebrand factor as a sensitive and distinctive marker for early (2N and 4N) megakaryocytes. Blood 2004; 104: 2722-2727

Tomer A, et al. Flow cytometric analysis of normal human megakaryocytes. Blood. 1988; 71:1244-1252.

Tomer A et al., Flow cytometric analysis of megakaryocytes from patients with abnormal platelet counts. Blood. 1989a; 74:594-601.

Tomer A. Effects of anagrelide on megakaryocyte proliferation and maturation in essential thrombocythemia. Blood, 2002:99:1602-1609.

Tomer A, et al., Purification of human megakaryocytes by fluorescence-activated cell sorting. Blood. 1987; 70:1735-1742.

J N George and M A Rizvi, Williams HEMATOLOGY, 6th Edition. Ernest Beutler et al editor. McGraw-Hill, Medical Publishing Division, 2001, Thrombocytopenia, Chapter 117, pp-1495-1540.

Tomer A, et al., Autologous platelet kinetics in patients with severe thrombocytopenia: discrimination between disorders of production and destruction. J Lab Clin Med. 1991; 118:546-554.

Neunert C et al., The American Society of Hematology 2011 evidence-based practice guideline for immune thrombocytopenia, Blood, 2011, April 21; 117(16):4190-207

Provan D et al., International consensus report on the investigation and management of primary immune thrombocytopenia, Blood 2010, January 14; 115(2):168-86.

Chong B H, Keng T B, Advances in the diagnosis of idiopathic thrombocytopenic purpura, Semin Hematol 2000, 37:249-260.

Cines D B, Blanchette V S: Immune thrombocytopenic purpura, N Engl J Med 2002, 346:995-1008.

McMillan R, et al., Prospective evaluation of the radioactive immunobead assay for the diagnosis of immune thrombocytopenic purpura (ITP). J Thromb Haemost 2003, 1:485-491.

Tomer A. et al., Menstrual cyclic thrombocytopenia. Br J. Haematol. 1989b; 71: 519-524.

McMillan R. et al., Suppression of In Vitro Megakaryocyte Production by Antiplatelet Autoantibodies from Adult Chronic ITP Patients. Blood 2004; 103:1364-1369.

Tomer A, et al., Autoimmune thrombocytopenia: Flow cytometric determination of circulating autoantibodies against platelet specific receptors. Journal of Thrombosis and Haemostasis. 2005; 3(1):74-78.

Miyakis S, et al., International consensus statement on an update of the classification criteria for definite antiphospholipid syndrome. J Thromb Haemost. 2006; 4(2):295-306).

Wong R C, Favaloro E J. A consensus approach to the formulation of guidelines for laboratory testing and reporting of antiphospholipid antibody assays. Semin Thromb Hemost. 2008 June; 34(4):361-72 de Groot Ph. G., presentation of Antiphospholipid syndrome, the International Society on Thrombosis & Haemostasis meeting, 7-10 Nov. 2011, in Cascais Portugal Merriman E, et al., Rivaroxaban and false positive lupus anticoagulant testing, Thromb Haemost. 2011 Feb. 1; 105(2):385-6.

Aboud M, False-negative or false-positive: laboratory diagnosis of lupus anticoagulant at the time of commencement of anticoagulant. J Thromb Haemost. 2010 September; 8(9):2070-3.

Pellegrino N M, Caccavo D., Variability in anticardiolipin antibody detection: role of nonspecific IgG binding and different microtiter plates, Clin Appl Thromb Hemosto. 2007 October; 13(4):404-9.

Bizzaro N et al., False-positive reactions for IgA antiphospholipid and anti-beta(2)-glycoprotein I antibodies in patients with IgA monoclonal gammopathy. Clin Chem. (1999) November; 45(11):2007-10.

Martorell J R et al., False positive activated protein C resistance test due to anti-phospholipid antibodies is corrected by platelet extract. Thromb Haemost. (1995).

Koike T et al., Anti-phospholipid antibodies and biological false positive serological test for syphilis in patients with systemic lupus erythematosus. Clin Exp Immunol. (1984) April; 56(1):193-9.

Rusnak J et al., False-positive rapid plasma reagin tests in human immunodeficiency virus infection and relationship to anti-cardiolipin antibody and serum immunoglobulin levels, J Infect Dis. 1994 June; 169(6):1356-9.

Lakos G, Teodorescu M., IgM, but not IgA rheumatoid factor interferes with anti-cardiolipin and antiβ2 glycoprotein I measurements: a quantitative analysis, Lupus. 2011 May; 20(6):614-9.

Moore G W, et al., Further evidence of false negative screening for lupus anticoagulants, Thromb Res. 2008; 121(4):477-84.

Pengo V et al., Survey of lupus anticoagulant diagnosis by central evaluation of positive plasma samples., J Thromb Haemost. 2007 May; 5(5):925-30.

de Larrañaga G et al., False positive reactions in confirmatory tests for syphilis in presence of antiphospholipid antibodies: misdiagnosis with prognostic and social consequences, Dermatol Online J. 2006 May 30; 12(4):22.

Asherson R A et al., Primary" antiphospholipid syndrome evolving into Waldenstrom's acroglobulinaemia: a case report, Clin Rheumatol. 2007 February; 26(2):278-80.

Zhu W F et al., Hepatitis C virus infection and biological false-positive syphilis test (and lupus anti-coagulant): a single-center experience, Hepatobiliary Pancreat Dis Int. 2011 August; 10(4):399-402.

Uthman I W et al., Infections and antiphospholipid antibodies, J Med Liban. 2000 September-October; 48(5):324-6.

Bernard C, et al., Biological true and false serological tests for syphilis: their relationship with anticardiolipin antibodies. Dermatologica. 1990; 180(3):151-3.

Sheridan D, et al., A diagnostic test for heparin-induced thrombocytopenia. Blood 1986; 67:27-30.

Kelton J G, et al., Heparin-induced thrombocytopenia: laboratory studies. Blood, 1988 September; 72(3):925-30.

Chong B H. Heparin-induced thrombocytopenia. Blood Rev 1988; 2(2): 108-114.

Alving B. Immune heparin-mediated thrombocytopenia and thrombosis. The Education Program of the American Society of Hematology. 1994. p 66-68.

Aster R H. Heparin-induced thrombocytopenia and thrombosis [editorial]. N Engl J Med 1995; 332:1374-1376.

Thielmann M et al. Perioperative thrombocytopenia in cardiac surgical patients—incidence of heparin-induced thrombocytopenia, morbidities and mortality. Eur J Cardiothorac Surg. 2010 June; 37(6):1391-5.

Arepally G, et al., Comparison of PF4/heparin ELISA assay with the 14 Cserotonin release assay in the diagnosis of HIT. Am J Clin Pathol 1995; 104:648-654.

Amiral J, et al, Presence of autoantibodies to interleukin-8 or neutrophil-activating peptide-2 in patients with heparin-associated thrombocytopenia. Blood. 1996 Jul. 15; 88(2): 410-6.

Hirsh J. et al., Heparin: mechanisms of action, pharmacokinetics, monitoring, efficacy, and safety. Chest 1995; 108: 258 S-275S.

Pauzner R, et al. False-positive tests for heparin-induced thrombocytopenia in patients with antiphospholipid syndrome and systemic lupus erythematosus. J Thromb Haemost. 2009 July; 7(7):1070-4.

Chong B H, et. The clinical usefulness of the platelet aggregation test for the diagnosis of heparin-induced thrombocytopenia. Thrombosis and Haemostasis, 1993, 69(4):344-50.

Visentin G P et al., Antibodies from patients with heparin-induced thrombocytopenia/thrombosis are specific for platelet factor 4 complexed with heparin or bound to endothelial cells. J Clin Invest 1994; 93:81-88.

Favoloro E J et al., Heparin-induced thrombocytopenia: laboratory investigation and confirmation of diagnosis. Pathology 1992; 24:177-183.

Tomer A. Rapid, sensitive and specific functional flow cytometric assay for the diagnosis of heparin-induced thrombocytopenia (HIT). Br J Haematol. 1997; 98(3): 648-656.

B S Coller and D L French, Hereditary Qualitative Platelet Disorders, Chapter 119, pp-1551-1582. In, Williams HEMATOLOGY, 6th Edition. Ernest Beutler et al editor. McGraw-Hill, Medical Publishing Division, 2001.

Nurden A, Nurden P. Advances in our understanding of the molecular basis of disorders of platelet function. J Thromb Haemost 2011 July; 9 Suppl 1:76-91.

Harold R Robert and Alice D Ma, Inherited platelet disorders. Chapter 58, page 883-885, In Hemostasis and Thrombosis: basic principles and clinical practice, Fifth Edition-Lippincott Williams & Wilkins 2006. Colman W Robert Editor.

Shattil S J et al., Acquired qualitative platelet disorders due to disease, drug and food, Chapter 120: pp-1583-1602. In, Williams HEMATOLOGY, 6th Edition. Ernest Beutler et al editor. McGraw-Hill, Medical Publishing Division, 2001).

Fitzgerald R, Pirmohamed M., Aspirin resistance: effect of clinical, biochemical and genetic factors. Pharmacol Ther. 2011 May; 130(2):213-25.

Qureshi Z, Hobson A R., Clopidogrel "Resistance": Where are We Now? Cardiovasc Ther. 2011 Aug. 3. doi: 10.1111/j.1755-5922.2011.00296.x. [Epub ahead of print]

The invention claimed is:

1. A method for diagnosis of Heparin-induced thrombocytopenia (HIT), comprising:
   stage A, comprising:
   1) incubating a first PI (patient 1) mixture, comprising an aliquot of the patient's serum or plasma sample, a platelet-rich plasma (PRP) of an individual not having a platelet-related pathology, and a physiologically-compatible buffer that does not contain a platelet activation agent and does not contain heparin;
   2) incubating a first PIH (patient 1 mixed with heparin) mixture, comprising an aliquot of the patient's serum or plasma sample, said PRP, said physiologically-compatible buffer that does not contain a platelet activation agent and does not contain heparin, and heparin;
   3) incubating a first NC (Normal Control) mixture, comprising an aliquot of a serum or plasma sample of an individual not having a platelet-related pathology, said PRP, and said physiologically-compatible buffer that does not contain a platelet activation agent and does not contain heparin; and
   4) incubating a first NCH (Normal Control mixed with heparin) mixture, comprising an aliquot of the serum or plasma sample of the individual not having a platelet-related pathology, said PRP, said physiologically-compatible buffer that does not contain a platelet activation agent and does not contain heparin, and heparin;
   stage B, comprising:
   1) incubating a second PI mixture, comprising an aliquot of the first PI mixture, a total platelet label that labels both total resting and heparin-activated platelet population, a heparin-activated platelet label that labels a population of platelets activated by antibodies in the presence of heparin, and said physiologically-compatible buffer that does not contain a platelet activation agent and does not contain heparin;
   2) incubating a second PIH mixture, comprising an aliquot of the first PIH sample, said total platelet label, said heparin-activated platelet label, and said physiologically-compatible buffer that does not contain a platelet activation agent and does not contain heparin;
   3) incubating a second NC mixture, comprising an aliquot of the first NC sample, said total platelet label, said heparin-activated platelet label, and said physiologically-compatible buffer that does not contain a platelet activation agent and does not contain heparin;
   4) incubating a second NCH mixture, comprising an aliquot of the first NCH sample, said total platelet label, said heparin-activated platelet label, and said physiologically-compatible buffer that does not contain a platelet activation agent and does not contain heparin; and
   Stage C, comprising:
   1) determining a platelet population in each of the second mixtures, by measuring the amount of labelled total platelet in each of the second mixtures;
   2) determining the degree of heparin activation of platelets among the determined platelet population in each of the second mixtures, by measuring the amount of labelled heparin-activated platelet in each of the second mixtures;

3) calculating a difference between the degree of heparin activation of platelets from the second PIH mixture and the degree of heparin activation of platelets from the second PI mixture;
4) calculating a difference between the degree of heparin activation of platelets from the second NCH mixture and the degree of heparin activation of platelets from the second NC mixture, and
5) comparing the difference calculated between the second PIH mixture and the second PI mixture with the difference calculated between the second NCH mixture and the second NC mixture,
wherein HIT is diagnosed in the patient's sample when the difference calculated between the second PIH mixture and the second PI mixture is substantially larger than the difference calculated between the second NCH mixture and the second NC mixture.

2. The method of claim 1, wherein the volume of the plasma or serum samples is not more than 10 µL.

3. The method of claim 1, wherein the incubation in Stage A is for about an hour and the incubation in Stage B is for about 15 minutes.

4. The method of claim 1, wherein the concentration of heparin in the first PIH and NCH is between 0.1 and 0.5 IU/mL.

5. The method of claim 4, wherein the concentration of heparin is about 0.3 IU/mL.

6. The method of claim 1, wherein the buffer is calcium and magnesium free Phosphate Buffered Saline.

7. The method of claim 1, wherein HIT is diagnosed when the difference calculated between the second PIH mixture and the second PI mixture is at least 2.5 times larger than the difference calculated between the second NCH mixture and the second NC mixture.

8. The method of claim 1, wherein the total platelet label is a fluorescence labeled monoclonal antibody against platelet receptor GPIIb/IIIa (CD41a) or CD61 expressed on both resting and heparin-activated platelets, and wherein each of the determining steps comprises measuring a specific fluorescence by the total platelet label bound to platelets.

9. The method of claim 8, wherein the first label is a fluorescence labeled monoclonal antibody anti-platelet CD41a(GPIIb/IIIa).

10. The method of claim 1, wherein the heparin-activated platelet label is a fluorescence labeled monoclonal antibody against p-selectin (CD62p) expressed by the heparin-activated platelets, and wherein each of the determining steps comprises measuring the intensity of fluorescence by the heparin-activated platelet label bound to heparin-activated platelets, wherein the fluorescence of the heparin-activated platelet label is distinguishable from the fluorescence of the total platelet label.

11. The method of claim 10, wherein said Stage C comprises:
1) measuring % of activated platelets in each of the second mixtures by setting a reference marker on a fluorescence of the heparin-activated platelet label to include platelets having a fluorescence comprising 2 Standard deviations (2SD) of Normal distribution of a high-CD62p-fluorescence end of the fluorescence measurement of the second NC mixture;
2) measuring with the same reference marker % of activated platelets in the second NCH, PI and PIH mixtures;
3) calculating the difference in reading of %-activated platelets between the second PIH mixture and the second PI mixture, and the difference in reading of %-activated platelets between the second NCH mixture and the second NC mixture, at said high-CD62p fluorescence end, and
4) comparing the difference between the second PIH mixture and the second PI mixture with the difference between the second NCH mixture and the second NC mixture,
wherein HIT is diagnosed in the patient's sample when the difference between the second PIH mixture and the second PI mixture is substantially larger than the difference between the second NCH mixture and the second NC mixture.

12. The method of claim 11, further comprising performance of an in vitro positive control assay for diagnosis of HIT,
wherein Stage B further comprises:
incubating a TRAP (a thrombin receptor agonist/activating peptide) mixture, comprising an aliquot of the first NC sample, a total platelet label, a heparin-activated platelet label, said buffer and TRAP;
and Stage C further comprises:
measuring the amount of heparin-activated platelets in the TRAP mixture by measuring the heparin-activated platelet label in the TRAP mixture, the measuring comprising measuring mean fluorescence of the heparin-activated platelet label and calculating the % of activated platelets from total platelet population.

13. The method of claim 11, wherein:
Stage A further comprises:
incubating a first PC (positive control) mixture, comprising: an aliquot of a plasma or serum sample of an individual having HIT, said PRP, and said buffer;
incubating a first PCH (positive control with heparin) mixture comprising: an aliquot of a plasma or serum sample of an individual having HIT, said PRP, said buffer, and heparin;
Stage B further comprises:
incubating a second PC mixture, comprising an aliquot of the first PC mixture, a total platelet label, a heparin-activated platelet label, and said buffer;
incubating a second PCH mixture, comprising an aliquot of the first PCH mixture, a total platelet label, a heparin-activated platelet label, and said buffer; and
Stage C further comprises:
measuring the amount of heparin-activated platelets in the second PC mixture and in the second PCH mixture by measuring mean fluorescence from the total platelet population and % of activated platelets; and
calculating a difference between the amount of heparin-activated platelets from the second PCH mixture and the amount of heparin-activated platelets from the second PC mixture.

14. The method of claim 10, wherein the degree of heparin activation of platelets is measured by the fluorescence intensity of the heparin-activated platelet label, wherein said calculating steps of, Stage C, 3) and 4) comprise:
calculating either the difference in mean fluorescence of CD62p in the total platelets, or the difference in amount of heparin-activated platelets located at a high-CD62p fluorescence end, between the second PIH mixture and the second PI mixture, and between the second NCH mixture and second NC mixture, and
said comparing step comprises:
comparing the difference calculated between the second PIH mixture and the second PI mixture with the difference calculated between the second NCH mixture and the second NC mixture,
wherein HIT is diagnosed in the patient's sample when the difference calculated between the second PIH mixture and the second PI mixture is substantially larger than the difference calculated between the second NCH mixture and the second NC mixture.

15. The method of claim 14, further comprising performance of an in vitro positive control assay for diagnosis of HIT,
wherein Stage B further comprises:
incubating a TRAP (a thrombin receptor agonist/activating peptide) mixture, comprising an aliquot of the first NC sample, a total platelet label, a heparin-activated platelet label, said buffer and TRAP;
and Stage C further comprises:
measuring the amount of heparin-activated platelets in the TRAP mixture by measuring the heparin-activated platelet label in the TRAP mixture, the measuring comprising measuring mean fluorescence of the heparin-activated platelet label and calculating the % of activated platelets from total platelet population.

16. The method of claim 14, wherein:
Stage A further comprises:
incubating a first PC (positive control) mixture, comprising: an aliquot of a plasma or serum sample of an individual having HIT, said PRP, and said buffer;
incubating a first PCH (positive control with heparin) mixture comprising: an aliquot of a plasma or serum sample of an individual having HIT, said PRP, said buffer, and heparin;
Stage B further comprises:
incubating a second PC mixture, comprising an aliquot of the first PC mixture, a total platelet label, a heparin-activated platelet label, and said buffer;
incubating a second PCH mixture, comprising an aliquot of the first PCH mixture, a total platelet label, a heparin-activated platelet label, and said buffer; and
Stage C further comprises:
measuring the amount of heparin-activated platelets in the second PC mixture and in the second PCH mixture by measuring mean fluorescence from the total platelet population and % of activated platelets; and
calculating a difference between the amount of heparin-activated platelets from the second PCH mixture and the amount of heparin-activated platelets from the second PC mixture.

17. The method of claim 10, wherein the platelet activation agent is selected from the group consisting of calcium and magnesium, and any combination thereof.

18. A kit for diagnosis of Heparin-induced thrombocytopenia (HIT), the kit comprising:
A. a physiologically-compatible buffer;
B. heparin,
C. a total platelet-specific antibody label,
D. a heparin-activated platelet-specific antibody label, and
E. TRAP, wherein the physiologically-compatible buffer does not contain a platelet activation agent.

* * * * *

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: synthetic

<400> SEQUENCE: 1

Leu Gly Gly Ala Lys Gln Ala Gly Asp Val
1               5                   10

<210> SEQ ID NO 2
<211> LENGTH: 6
<212> TYPE: PRT
<213> ORGANISM: Artificial Sequence
<220> FEATURE:
<223> OTHER INFORMATION: synthetic

<400> SEQUENCE: 2

Lys Gln Ala Gly Asp Val
1               5
```